(12) United States Patent
Sterling et al.

(10) Patent No.: US 6,862,534 B2
(45) Date of Patent: Mar. 1, 2005

(54) METHOD OF DETERMINING AN ANALYTE CONCENTRATION IN A SAMPLE FROM AN ABSORPTION SPECTRUM

(75) Inventors: Bernhard B. Sterling, Sunnyvale, CA (US); James R. Braig, Piedmont, CA (US); Daniel S. Goldberger, Boulder, CO (US); Philip C. Hartstein, Cupertino, CA (US); Robert D. Gaffney, Atherton, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 0 days.

(21) Appl. No.: 10/366,540

(22) Filed: Feb. 12, 2003

(65) Prior Publication Data

US 2004/0019431 A1 Jan. 29, 2004

Related U.S. Application Data

(63) Continuation-in-part of application No. 10/319,409, filed on Dec. 12, 2002.
(60) Provisional application No. 60/341,435, filed on Dec. 14, 2001, and provisional application No. 60/357,264, filed on Feb. 12, 2002.

(51) Int. Cl.$^7$ .............................................. G06F 19/00
(52) U.S. Cl. ......................................... 702/23; 702/22
(58) Field of Search ............................. 702/22, 23, 31, 702/3; 435/39; 600/310, 322

(56) References Cited

U.S. PATENT DOCUMENTS

| | | |
|---|---|---|
| 3,787,124 A | 1/1974 | Lowy et al. |
| 4,350,441 A | 9/1982 | Wicnienski |
| 4,397,956 A | 8/1983 | Maggio |
| 4,655,225 A | 4/1987 | Dähne et al. |
| 4,730,112 A | 3/1988 | Wong |
| 4,819,752 A | 4/1989 | Zelin |
| 5,081,998 A | 1/1992 | Yelderman et al. |
| 5,111,817 A | 5/1992 | Clark et al. |

(List continued on next page.)

FOREIGN PATENT DOCUMENTS

| | | |
|---|---|---|
| EP | 0 982 582 A1 | 8/1998 |
| EP | 0982582 A1 | 3/2000 |
| WO | WO 93/13706 | 7/1993 |
| WO | WO 99/39631 | 8/1999 |
| WO | WO 01/30236 | 5/2001 |
| WO | PCT/US 02/40133 | 12/2002 |
| WO | PCT/US 03/04548 | 9/2003 |

OTHER PUBLICATIONS

Kajiwara, K; Fukushima, H; Kishikawa, H; Nishida, K; Hashiguchi, Y; Sakakida, M; Uchara, M; Shichiri, M;("Spectroscopic Quantitative Analysis of Blood Glucose by Fourier Transform Infrared Spectroscopy with an Attenuated Total Reflection Prism"; Medical Progress Through Technology No. 3; 1992; pp 181–189.*

(List continued on next page.)

*Primary Examiner*—John Barlow
*Assistant Examiner*—Douglas N Washburn
(74) *Attorney, Agent, or Firm*—Knobbe, Martens, Olson & Bear, LLP

(57) ABSTRACT

A method determines an analyte concentration in a sample including the analyte and a substance. The method includes providing an absorption spectrum of the sample. The absorption spectrum has an absorption baseline. The method further includes shifting the absorption spectrum so that the absorption baseline approximately equals a selected absorption value in a selected absorption wavelength range. The method further includes subtracting a substance contribution from the absorption spectrum. Thus, the method provides a corrected absorption spectrum substantially free of a contribution from the substance.

28 Claims, 22 Drawing Sheets

U.S. PATENT DOCUMENTS

| | | | |
|---|---|---|---|
| 5,204,532 | A | 4/1993 | Rosenthal |
| 5,277,181 | A | 1/1994 | Mendelson et al. |
| 5,348,003 | A | 9/1994 | Caro |
| 5,361,758 | A | 11/1994 | Hall et al. |
| 5,370,114 | A | 12/1994 | Wong et al. |
| 5,372,136 | A | 12/1994 | Sterner et al. |
| 5,377,674 | A | 1/1995 | Kuestner |
| 5,379,764 | A | 1/1995 | Barnes et al. |
| 5,412,581 | A | 5/1995 | Tackett |
| 5,452,716 | A | 9/1995 | Clift |
| 5,481,113 | A | 1/1996 | Dou et al. |
| 5,576,544 | A | 11/1996 | Rosenthal |
| 5,606,164 | A | 2/1997 | Price et al. |
| 5,655,530 | A | 8/1997 | Messerschmidt |
| 5,692,503 | A | 12/1997 | Kuenstner |
| 5,713,353 | A | 2/1998 | Castano |
| 5,720,284 | A | 2/1998 | Aoyagi et al. |
| 5,725,480 | A | 3/1998 | Oosta et al. |
| 5,773,301 | A | 6/1998 | Ziegler |
| 5,823,951 | A | 10/1998 | Messerschmidt |
| 5,857,462 | A | 1/1999 | Thomas et al. |
| 5,900,632 | A | 5/1999 | Sterling et al. |
| 5,933,792 | A * | 8/1999 | Andersen et al. ............ 702/32 |
| 6,040,578 | A | 3/2000 | Malin et al. |
| 6,067,463 | A | 5/2000 | Jeng et al. |
| 6,087,182 | A | 7/2000 | Jeng et al. |
| 6,115,673 | A | 9/2000 | Malin et al. |
| 6,121,050 | A | 9/2000 | Han |
| 6,124,134 | A | 9/2000 | Stark |
| 6,157,041 | A | 12/2000 | Thomas et al. |
| 6,161,028 | A | 12/2000 | Braig et al. |
| 6,198,949 | B1 | 3/2001 | Braig et al. |
| 6,236,047 | B1 | 5/2001 | Malin et al. |
| 6,262,798 | B1 | 7/2001 | Shepard et al. |
| 6,285,448 | B1 | 9/2001 | Kuenstner |
| 6,426,045 | B1 | 7/2002 | Jeng et al. |
| 6,580,934 | B1 | 6/2003 | Braig et al. |
| 2003/0031597 | A1 * | 2/2003 | Sota et al. ............... 422/82.09 |

OTHER PUBLICATIONS

Sim, B; Tong, Y; Chang, J; Tan, C; "A Parametric Formulation of the Generalized Spectral Subtraction Method"; IEEE Transactions on Speech and Audio Processing; vol. 6, Is 4; Jun. 1998; pp 328–337.*

Percherancier, J; Vuarchex, P; "Fourier Transform Infrared (FT–IR) Spectrometry to Detect Additives an Contaminants in Insulating Oils"; IEEE Electrical Insulation Magazine; vol. 14, Is 3; May–Jun. 1998; pp 23–29.*

Ham, F; Kostanic, I; Cohen, G; Gooch, B; "Determination of Glucose Concetrations in an Aqueous Matrix from Spectra Using Optimal Time–Domain Filtering and Partial Least– Squares Regression"; IEEE Trans. Biomed. Eng.; vol. 44, Is 6; Jun. 1998; pp 475–485.*

Ken–ichiro Kajiwara et al., *Spectroscopic quantitative analysis of blood glucose by Fourier transform infrared spectroscopy with an attenuated total reflection prism,* Medical Progress through Technology 18, No. 3 (1992), pp. 181–189.

Burmeister, Jason J., et al., *Spectroscopic Considerations for Noninvasive Blood Glucose Measurements with Near Infrared Spectroscopy,* IEEE Infrared Spectroscopy Newsletter, Apr. 1998, pp 1–5.

Heise, H.M., *Multicomponent Assay for Blood Substrates in Human Plasma by Mid–Infrared Spectroscopy and its Evaluation for Clinical Analysis,* Applied Spectroscopy, vol. 48, No. 1, 1994, pp 85–95.

Janatsch, Günter, et al., *Multivariate Calibration for Assays in Clinical Chemistry Using Attenuated Total Reflection Infrared Spectra of Human Blood Plasma,* Analytical Chemistry, 1989, vol. 61, pp 2016–2023.

Kajiwara, Ken–ichiro, et al., *Spectroscopic Quantitative Analysis of Blood Glucose by Fourier Transform Infrared Spectroscopy with an Attenuated Total Reflection Prism,* Medical Progress through Technology, vol. 18, No. 3, 1992, Dordrecht, NL, pp 181–189.

Kuenstner, J. Todd, et al., *Spectrophotometry of Human Hemoglobin in the Midinfrared Region,* 1997, pp 225–232.

Lewis, Christopher B., et al., *Investigation of Near–Infrared Spectroscopy for Periodic Determination of Glucose in Cell Culture Media in Situ,* Applied Spectroscopy, vol. 54, No. 10, 2000, pp 1453–1457.

McShane, Michael J., et al, *Near–Infrared Spectroscopy for Determination of Glucose, Lactate, and Ammonia in Cell Culture Media,* Applied Spectroscopy, vol. 52, No. 8, 1998, pp 1073–1078.

Mirouze, F. De Lène, et al., *Quantitative Analysis of Glucose Syrups by ATR/FT–IR Spectroscopy,* Applied Spectroscopy, vol. 47, No. 8, 1993, pp 1187–1191.

Norris, K.H., et al., *Rapid Measurement of Analytes in Whole Blood with NIR Transmittance, Leaping Ahead with Near Infrared Spectroscopy,* 1995, pp 432–436.

Petibois, Cyril, et al., *Glucose and Lactate Concentration Determination on Single Microsamples by Fourier–Transform Infrared Spectroscopy,* INSERM U 443, Equipe deChimie Bio–Organique, Oct. 1999, pp 210–215.

Shaw, R. Anthony, et al., *Infrared Spectroscopy in Clinical and Diagnostic Analysis,* Encyclopedia of Analytical Chemistry, pp 1–20.

Ward, Kenneth J., et al., *Post–Prandial Blood Glucose Determination by Quantitative Mid–Infrared Spectroscopy,* Applied Spectroscopy, vol. 46, No. 6, 1992, pp 959–965.

* cited by examiner

Mixtures

METHOD OF DETERMINING AN ANALYTE CONCENTRATION IN A SAMPLE FROM AN ABSORPTION SPECTRUM

RELATED APPLICATIONS

The present application is based upon and claims priority under 35 U.S.C. § 119(e) to U.S. Provisional Application No. 60/357,264, filed Feb. 12, 2002, which is incorporated in its entirety by reference herein. The present application is also a continuation-in-part from and claims priority under 35 U.S.C. § 120 to U.S. patent application Ser. No. 10/319,409, filed Dec. 12, 2002, incorporated in its entirety by reference herein, and which was based on and claimed priority under 35 U.S.C. § 119(e) to U.S. Provisional Patent Application No. 60/341,435 filed Dec. 14, 2001 and U.S. Provisional Patent Application No. 60/357,264 filed Feb. 12, 2002.

BACKGROUND OF THE INVENTION

1. Field of the Invention

The disclosure herein relates generally to methods for determining the composition of a material sample by analyzing electromagnetic energy that has passed through or has been emitted from the material sample.

2. Description of the Related Art

A large number of people suffer from diabetes and other conditions in which the natural regulation of blood glucose levels is impaired. For these people, monitoring blood glucose level is an important part of health maintenance, and a variety of techniques and instruments have been developed to periodically measure glucose levels in blood samples for this purpose.

Most of these methods involve a spectroscopic measurement, where the absorption of electromagnetic energy of a blood sample is measured and correlated to glucose concentration. In some cases, the electromagnetic energy is at optical wavelengths. In these systems, a chemical reagent is typically added to the blood sample which chemically reacts with the glucose and produces an absorption in the optical band dependent on the amount of glucose present and which participates in the reaction. In addition to the expense of manufacturing such reagent based systems, these assays may be interfered with by other blood constituents that reduce their accuracy and reproducibility.

Although reagent based optical assays have been successfully produced and commercialized, blood absorption characteristics in the infrared (IR) region of the electromagnetic spectrum have been recently explored to measure blood glucose concentrations. This has advantages over optical wavelength measurements since glucose exhibits significant absorption in several IR wavelength regions without the need to perform a reaction with another chemical species that must be added to the blood sample.

However, other chemical species including water, alanine, albumin, hemoglobin, urea, lactate and others also absorb strongly at several IR band frequencies. Some of these constituents are present in the blood at concentrations of 50 or 100 times or more than the glucose concentration. Because the sample absorption at any given wavelength is a sum of the absorptions of each component at that wavelength, IR absorption measurements are complicated by the presence of these other components. Consequently, methods that allow effective compensation and adjustments to measured IR absorption for the presence of other blood components would be beneficial to provide a low cost and accurate system for diabetics and others in need of periodic glucose monitoring.

SUMMARY OF THE INVENTION

In accordance with certain embodiments described herein, a method determines an analyte concentration in a sample comprising the analyte and a substance. The method comprises providing an absorption spectrum of the sample. The absorption spectrum has an absorption baseline. The method further comprises shifting the absorption spectrum so that the absorption baseline approximately equals a selected absorption value in a selected absorption wavelength range. The method further comprises subtracting a substance contribution from the absorption spectrum. Thus, the method provides a corrected absorption spectrum substantially free of a contribution from the substance.

In accordance with other embodiments described herein, a method provides pathlength-insensitive measurements of blood constituents in a sample using infrared (IR) spectroscopy. The method comprises providing an absorption spectrum of the sample. The absorption spectrum has an absorption baseline. The method further comprises shifting the absorption spectrum so that the absorption baseline approximately equals a selected absorption value in an absorption wavelength range comprising an isosbestic wavelength at which water and a whole blood protein have approximately equal absorptions.

In accordance with still other embodiments described herein, a method measures a pathlength of a sample comprising a first component and a second component. The method comprises providing an absorption spectrum of the sample. The method further comprises determining an absorption value of the absorption spectrum at an isosbestic wavelength at which the first component and the second component have approximately equal absorptions. The method further comprises calculating the pathlength from the absorption value.

In accordance with still other embodiments described herein, a method estimates a glucose concentration of a blood sample. The method comprises measuring sample absorption at a plurality of wavelengths between about 4 microns and 11 microns. The method further comprises subtracting a contribution to said sample absorption due to the presence of water. The method further comprises subtracting a contribution to said sample absorption due to the presence of hemoglobin.

For purposes of summarizing the invention, certain aspects, advantages and novel features of the invention have been described herein above. It is to be understood, however, that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION

As will be described further below, absorption data (sometimes called "optical density" or "OD") from a sample can be used to determine the relative concentrations of the various constituents of the sample. In particular, infrared absorption data from a blood sample can be used to determine the concentrations of various analytes. A specific technique for measuring glucose concentration is described herein, but it will be appreciated that the techniques described below could be used to measure whole blood proteins, urea, lactate, or other sample analytes.

In many measurements, the contribution from the analyte of interest (e.g., glucose) to the measured absorption spectrum is often only a small percentage of the contribution from other substances within the sample. For example, blood by volume is typically composed of about 70% water, about 30% solids, mostly protein, and only about 0.1% glucose. Blood also includes other species such as urea, alanine, and in some cases alcohol or other sugars such as fructose. Therefore, blood glucose measurements are highly sensitive and vulnerable to inaccuracies.

If an accurate glucose measurement is desired, the characteristics of each of the different blood constituents should be considered. In an attempt to avoid the large absorption due to water, previous efforts have focused on the near-infrared (IR) region (e.g., wavelengths less than about 2.5 microns). In the near-IR region, the IR absorption of water is quite small. However, many blood components such as alanine, urea, albumin, ascorbate, and triacetin have absorptions of similar magnitude to glucose, and although attempts have been made, separating their relative contributions is difficult.

Figure 1A:
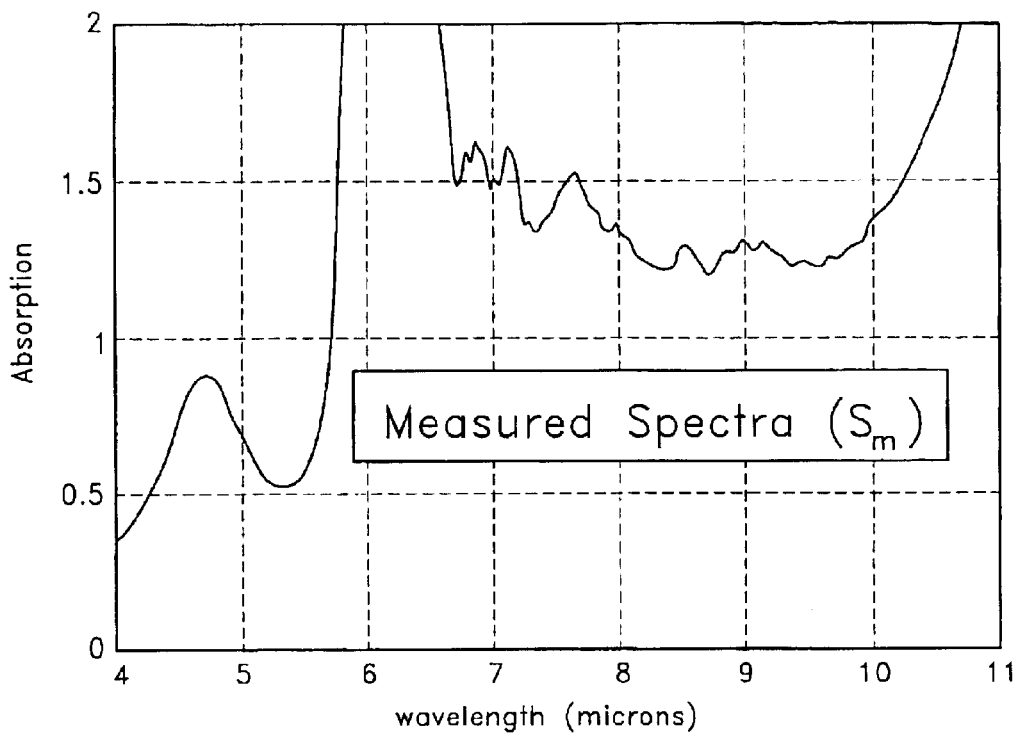
FIGS. 1A and 1B illustrate absorption plots of blood and pure water, respectively, in the wavelength range of about 4 to about 11 microns.
Figure 1B:
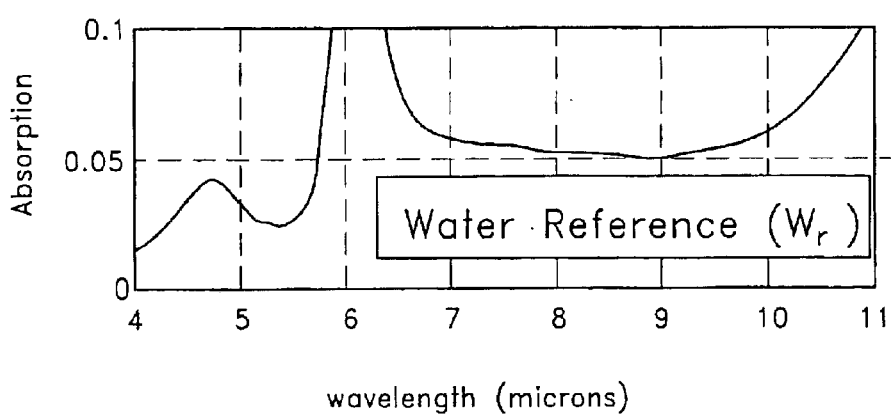

Advantageously, the system and method described herein utilize absorption data in the mid-IR region of about 4 to about 11 microns, and a procedure for subtraction of the contribution due to water. FIG. 1A illustrates an absorption plot of blood at these wavelengths and FIG. 1B illustrates an absorption plot of pure water. Although the main contributor to the total absorption is water across this spectrum, the peaks and other structure present in the blood spectrum from about 6.8 microns to 10.5 microns are due to the combination of the absorption spectra of other blood components. The 4 to 11 micron region has been found advantageous because glucose has a strong absorption peak structure from about 8.5 to 10 microns, whereas most other blood constituents have a low and flat absorption spectrum in the 8.5 to 10 micron range. The main exceptions are water and hemoglobin, both of which absorb fairly strongly in this region, and which are also the two most significant blood components in terms of concentration. Certain embodiments of the technique described herein are thus directed to removing the contributions of water and hemoglobin from this region to resolve the contribution, and thus concentration, of glucose in the sample.

Figure 2:
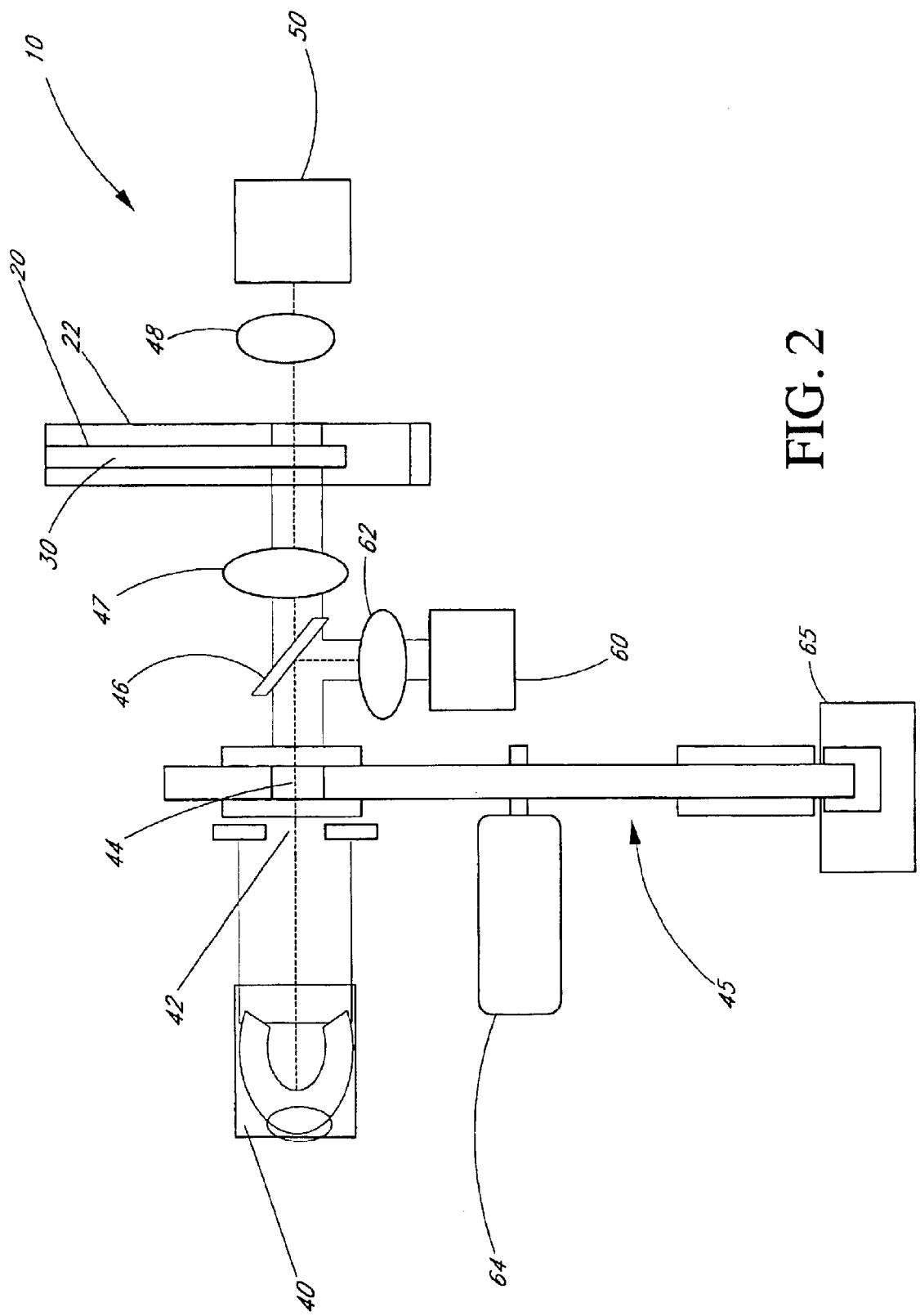
FIG. 2 schematically illustrates one configuration for providing a transmittance spectrum from which the absorption spectrum is obtained.

FIG. 2 schematically illustrates one configuration 10 compatible with embodiments described herein for providing a transmittance spectrum from which the absorption spectrum is obtained. The configuration 10 comprises a cuvette 20 within a cassette 22, the cuvette 20 containing the sample 30. The cuvette 20 is substantially transparent to infrared radiation in the wavelength range under analysis. In certain embodiments, the sample 30 comprises blood and the analyte comprises glucose. The configuration 10 also includes an infrared source 40, an aperture 42, a filter 44 on a filter wheel 45, a beam splitter 46, a sample lens 47, a signal lens 48, an infrared signal detector 50, an infrared reference detector 60, and a reference lens 62. One example of an instrument compatible with embodiments described herein is a Fourier-Transform Infrared (FTIR) spectrometer available from Perkin-Elmer, Inc. of Wellseley, Mass.

As illustrated by FIG. 2, the cuvette 20 is positioned between the infrared source 40 and the infrared signal detector 50, such that at least a portion of an infrared signal emitted from the source 40 is transmitted through the cuvette 20 and sample 30, and is measured by the signal detector 50. The infrared source 40 is adapted to provide an infrared signal comprising a plurality of wavelengths. In certain embodiments, as illustrated in FIG. 2, the source 40 provides a broadband infrared signal in which the plurality of wavelengths are emitted concurrently and are transmitted through the aperture 42 and the filter 44 to select a particular wavelength. In other embodiments, the source 40 is tunable to provide an infrared signal with a selected wavelength.

The aperture 42 of certain embodiments defines the beam size of the infrared signal which is incident onto the filter 44. As illustrated in FIG. 2, the filter 44 in certain embodiments is one of a plurality of filters on a filter wheel 45. The filter wheel 45 comprises a stepper motor 64 and a position sensor 65 so that the filter wheel 45 can be rotated in order to place a selected filter 44 in the path of the infrared signal.

The infrared signal transmitted through the filter 44 is split by the beam splitter 46 into two separate portions, propagating along two separate paths. Along the signal path, the signal portion of the infrared signal is focused onto the sample 30 by the sample lens 47. The portion of the signal portion transmitted through the sample 30 is focused onto the signal detector 50 by the signal lens 48. Along the reference path, the reference portion of the infrared signal is focused onto the reference detector 60 by the reference lens 62.

In certain embodiments, the signal detector 50 and reference detector 60 concurrently measure infrared radiation of a plurality of wavelengths, while in other embodiments, the detectors 50, 60 are tunable to measure a selected wavelength. The signal detected by the reference detector 60 can be used to correct the signal detected by the signal detector 50 for variations in the emitted signal from the source 40. In addition, in embodiments in which the reference detector 60 and signal detector 50 are substantially identical, the reference detector 60 can be used to correct for a wavelength-dependent response of the signal detector 50.

Figure 3:
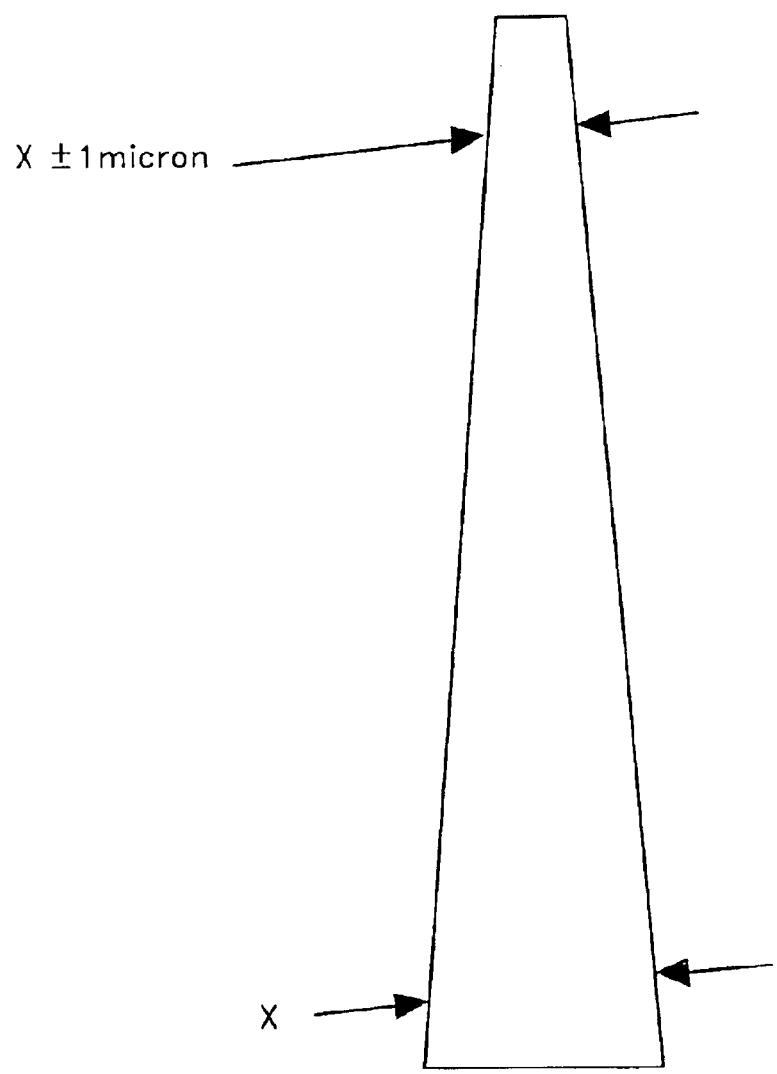
FIG. 3 schematically illustrates the planarity of a cuvette.

FIG. 3 schematically illustrates the planarity design specification of the cuvette 20. To ensure that the signal detected by the signal detector 50 is not dependent on the location on the cuvette 20 through which the infrared signal propagates, the cuvette 20 preferably has a sufficient degree of planarity between its two surfaces. In preferred embodiments, the planarity is within ±1 micron. This plurality can be achieved using rigid materials for the cuvette 20, and exemplary materials include, but are not limited to, silicon and $BaF_2$.

Figure 4:
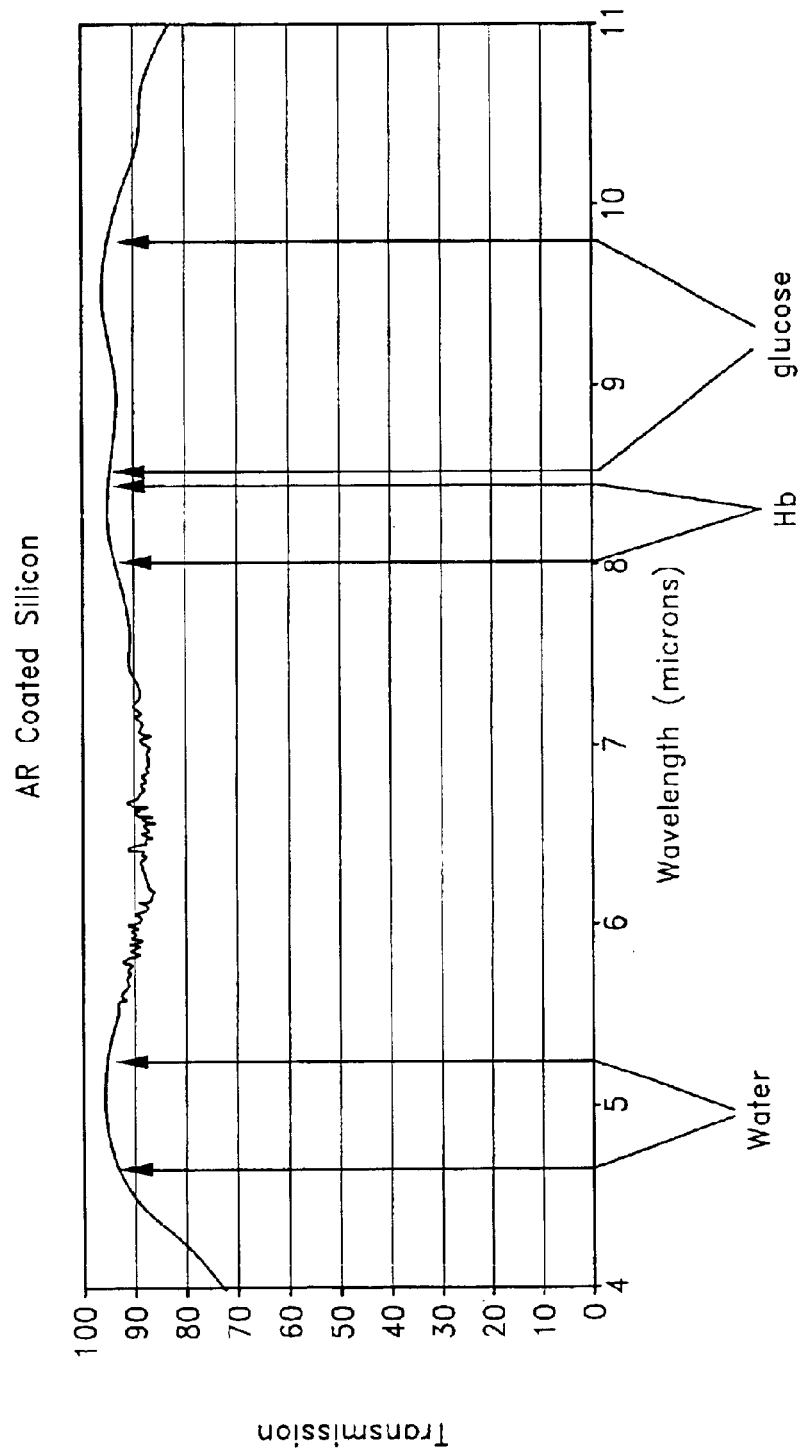
FIG. 4 is a graph of the transmission spectrum of AR-coated silicon for wavelengths between 4 and 11 microns.

The transmittance design specification of the cuvette 20 is schematically illustrated by FIG. 4. To avoid loss of signal by absorption by the cuvette 20 itself, the material of the cuvette 20 is preferably selected to have a relatively high transmittance in the wavelength range of interest. Exemplary materials include, but are not limited to, silicon. FIG. 4 shows that the transmission of AR-coated silicon is greater than 90% in the wavelength ranges of approximately 4.5–5.5 microns and 7.9–10.1 microns.

Another cuvette material compatible with embodiments described herein is polyethylene, which can provide a cost-effective option. Polyethylene can be used to form the cuvette 20 by a variety of techniques including, but not limited to, injection molding technology and laminar "web" assembly technology.

Figure 5:
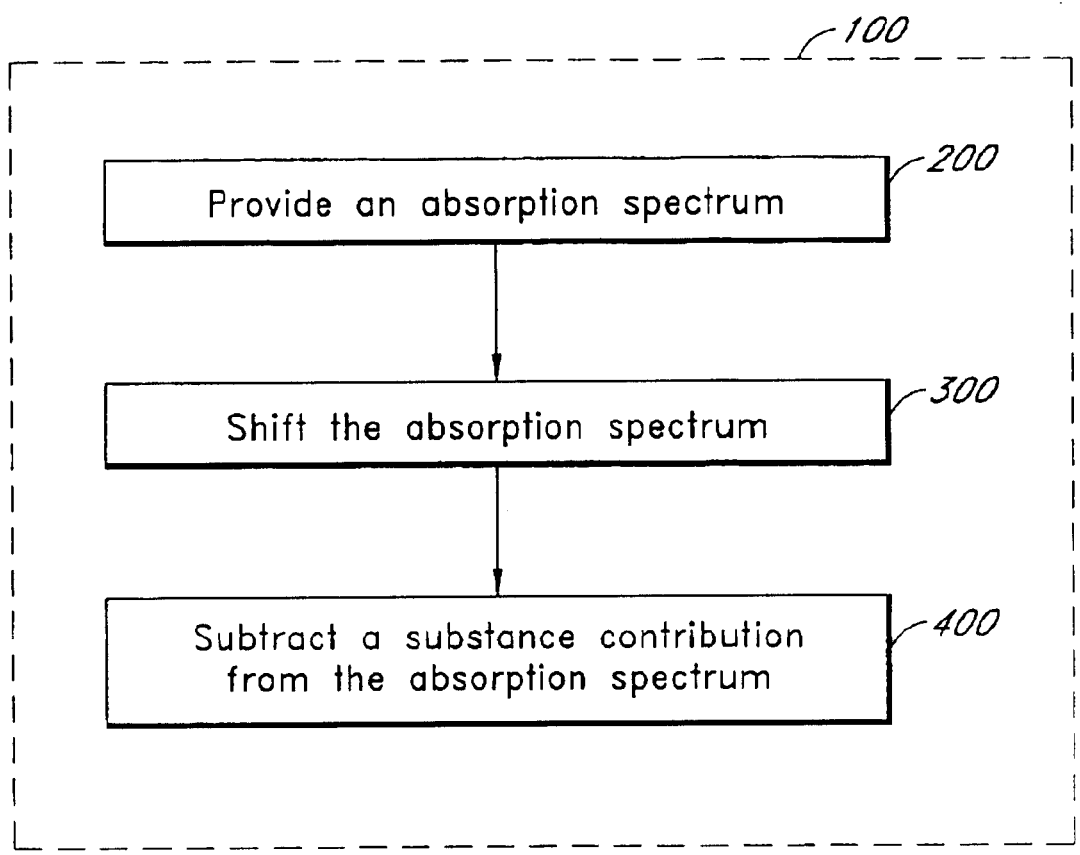
FIG. 5 is a flow diagram of one embodiment of a method of determining an analyte concentration in a sample.

FIG. 5 is a flow diagram of one embodiment of a method 100 of determining an analyte concentration in a sample comprising the analyte and a substance. The method 100 comprises providing an absorption spectrum of the sample, with the absorption spectrum having an absorption baseline in an operational block 200. The method 100 further comprises shifting the absorption spectrum so that the absorption baseline approximately equals a selected absorption value in a selected absorption wavelength range in an operational block 300. The method 100 further comprises subtracting a substance contribution from the absorption spectrum in an operational block 400. Thus, the method 100 provides a corrected absorption spectrum substantially free of a contribution from the substance.

Figure 6:
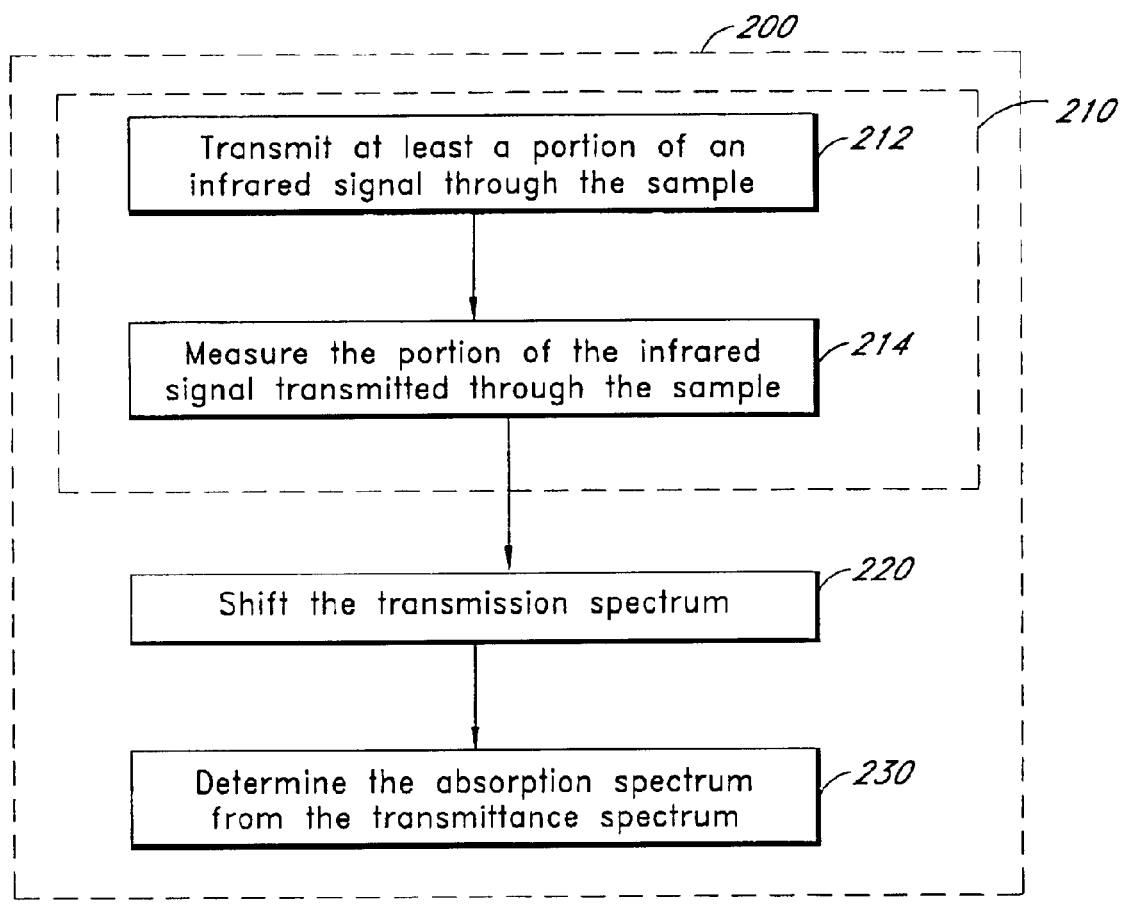
FIG. 6 is a flow diagram of one embodiment for providing the absorption spectrum.

In certain embodiments, providing the absorption spectrum in the operational block 200 comprises irradiating the sample 30 with infrared radiation and measuring the absorption of the infrared radiation by the sample 30 as a function of the wavelength or energy of the infrared radiation. FIG. 6 is a flow diagram of one embodiment for providing the absorption spectrum in the operational block 200 of FIG. 5.

Figure 7A:
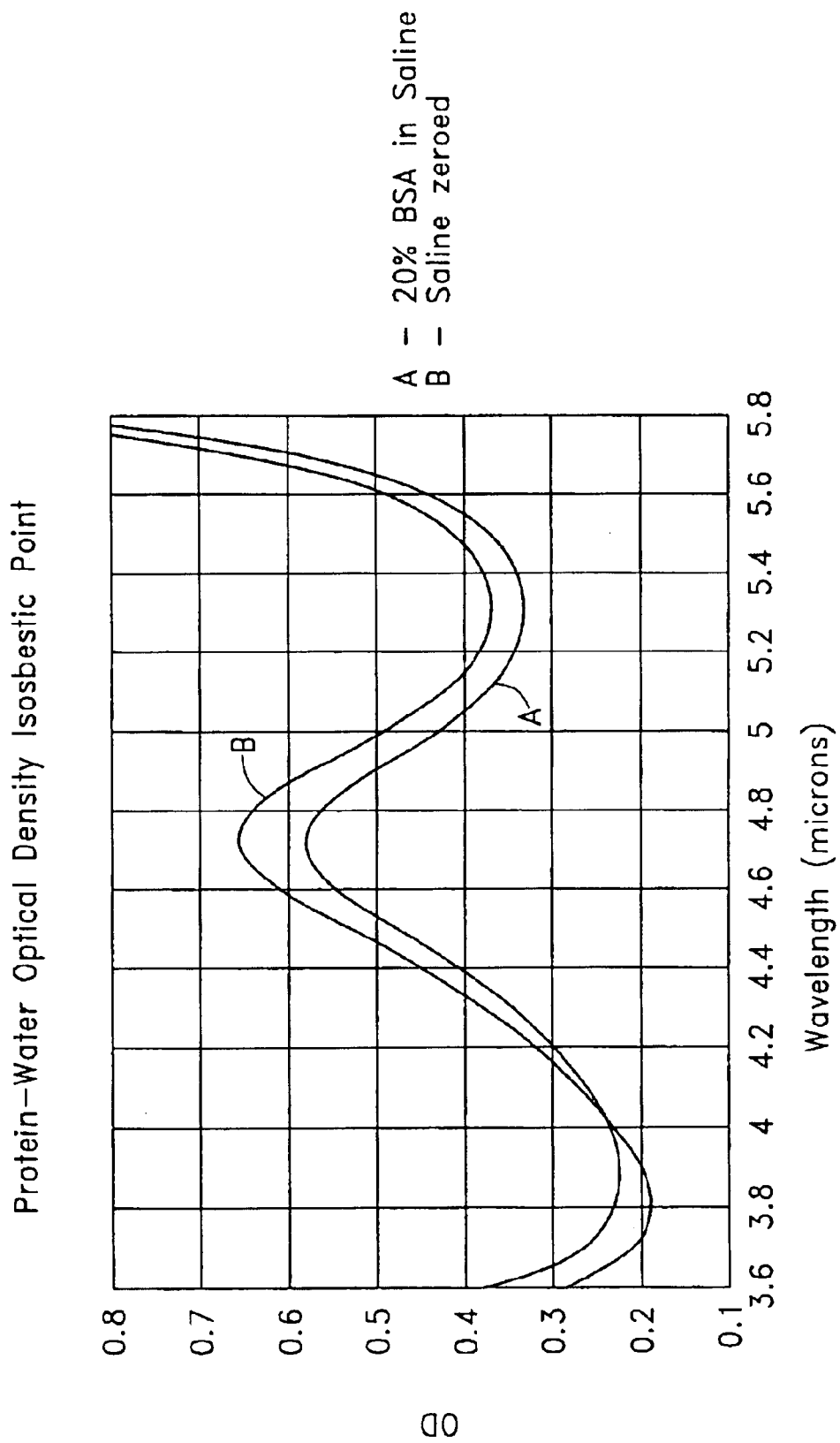
FIGS. 7A and 7B are graphs of the absorption spectra for 20% BSA in saline and for saline alone in two wavelength ranges.

In an operational block 210, the transmittance spectrum of the sample 30 is provided, with the transmittance spectrum having a transmittance baseline. In certain embodiments, the transmittance spectrum of the sample 30 is provided by transmitting at least a portion of an infrared signal through the sample 30 in an operational block 212. The infrared signal comprises a plurality of wavelengths. The portion of the infrared signal transmitted through the sample 30 is measured as a function of wavelength in an operational block 214. While the configuration 10 illustrated in FIG. 2 can be used to provide the transmittance spectrum, other configurations and devices can also be used to provide the transmittance spectrum in accordance with embodiments described herein. FIG. 7A schematically illustrates an exemplary transmittance spectrum for a sample 30 comprising blood in accordance with embodiments described herein.

In certain embodiments, the transmittance baseline is defined to be the value of the transmittance spectrum at wavelengths at which transmittance is a minimum. For blood, this value is typically at about 6.1–6.2 microns where water and hemoglobin both are strong absorbers. While the transmittance spectrum from the sample 30 at these wavelengths is expected to be nearly zero, various effects, such as instrumental error and thermal drift, can result in a nonzero contribution to the transmittance baseline. In addition, effects such as instrumental error and thermal drift can result in a wavelength shift of known features in the transmittance spectrum from the expected wavelengths of these features.

In certain such embodiments, as illustrated in the operational block 220 of FIG. 6, providing the absorption spectrum in the operational block 200 comprises shifting the transmittance spectrum so that the transmittance baseline approximately equals zero in a selected transmittance wavelength range. In certain embodiments in which the sample 30 comprises blood, the selected transmittance wavelength range comprises wavelengths at which the transmittance is a minimum. In certain such embodiments, the selected transmittance wavelength range comprises wavelengths between approximately 6 microns and approximately 6.15 microns. In other such embodiments, the selected transmittance wavelength range comprises wavelengths between approximately 12 microns and approximately 13 microns. The transmittance spectrum at these wavelengths may be partially affected by contributions from various blood components that are present at low concentration levels. In still other such embodiments, the selected transmittance wavelength range comprises wavelengths approximately equal to 3 microns. Each of these wavelengths is corresponds to a strong water absorption peak.

In embodiments in which there is a nonzero contribution to the transmittance baseline, the transmittance spectrum may be shifted. In certain embodiments, the transmittance spectrum is shifted so that the transmittance spectrum in the wavelength range of 6 to 6.2 microns is approximately equal to zero. In embodiments in which known features are shifted in wavelength from their expected wavelengths, the transmittance spectrum can be shifted in wavelength. In addition, the shifting of the transmittance spectrum can be performed nonlinearly (e.g., shifting different wavelengths by differing amounts across the transmittance spectrum).

As illustrated by FIG. 6, providing the absorption spectrum further comprises determining the absorption spectrum from the transmittance spectrum in an operational block 230. In certain embodiments, the relation between the transmittance spectrum and the absorption spectrum is expressed as:

$$A(\lambda) = \ln\left(\frac{1}{T(\lambda)}\right)$$

where $\lambda$ is the wavelength, $A(\lambda)$ is the absorption as a function of wavelength, and $T(\lambda)$ is the transmittance as a function of wavelength.

As shown by the operational block 300 of FIG. 5, in certain embodiments, the method 100 comprises shifting the absorption spectrum so that its absorption baseline approximately equals a selected absorption value in a selected absorption wavelength range. In certain embodiments, the absorption baseline can be selected to be defined by a portion of the absorption spectrum with low absorption. In certain other embodiments in which the sample 30 comprises blood, the absorption baseline is defined to be the magnitude of the absorption spectrum at an isosbestic wavelength at which water and a whole blood protein have approximately equal absorptions. Exemplary whole blood proteins include, but are not limited to, hemoglobin, albumin, globulin, and ferritin.

In an exemplary embodiment to illustrate the isosbestic wavelengths, blood was simulated in its major components using bovine serum albumin (BSA) for whole blood protein and saline for serum. Infrared absorption spectra of the samples were measured with a Perkin-Elmer FTIR instrument. Cuvette pathlength was set with different spacers between $BaF_2$ windows at 32 and 20 micrometers. The fringe pattern of the empty cuvette was used for calculation of the actual optical pathlength inside the cuvette. Flexible tubing and the flow-through type of the cuvette allowed for repeated filling with different solutions without changes being made to the experimental setup. Instrumental drift and baseline deviations were accounted for with saline reference measurements before and after sample measurements. A total of 100 scans were collected per sample over a period of about 5 minutes. Scanned data were stored in ASCII format and transferred to an electronic spreadsheet program (e.g., Lotus 1-2-3 from IBM Corp. of Armonk, N.Y.) for evaluation.

Figure 7B:
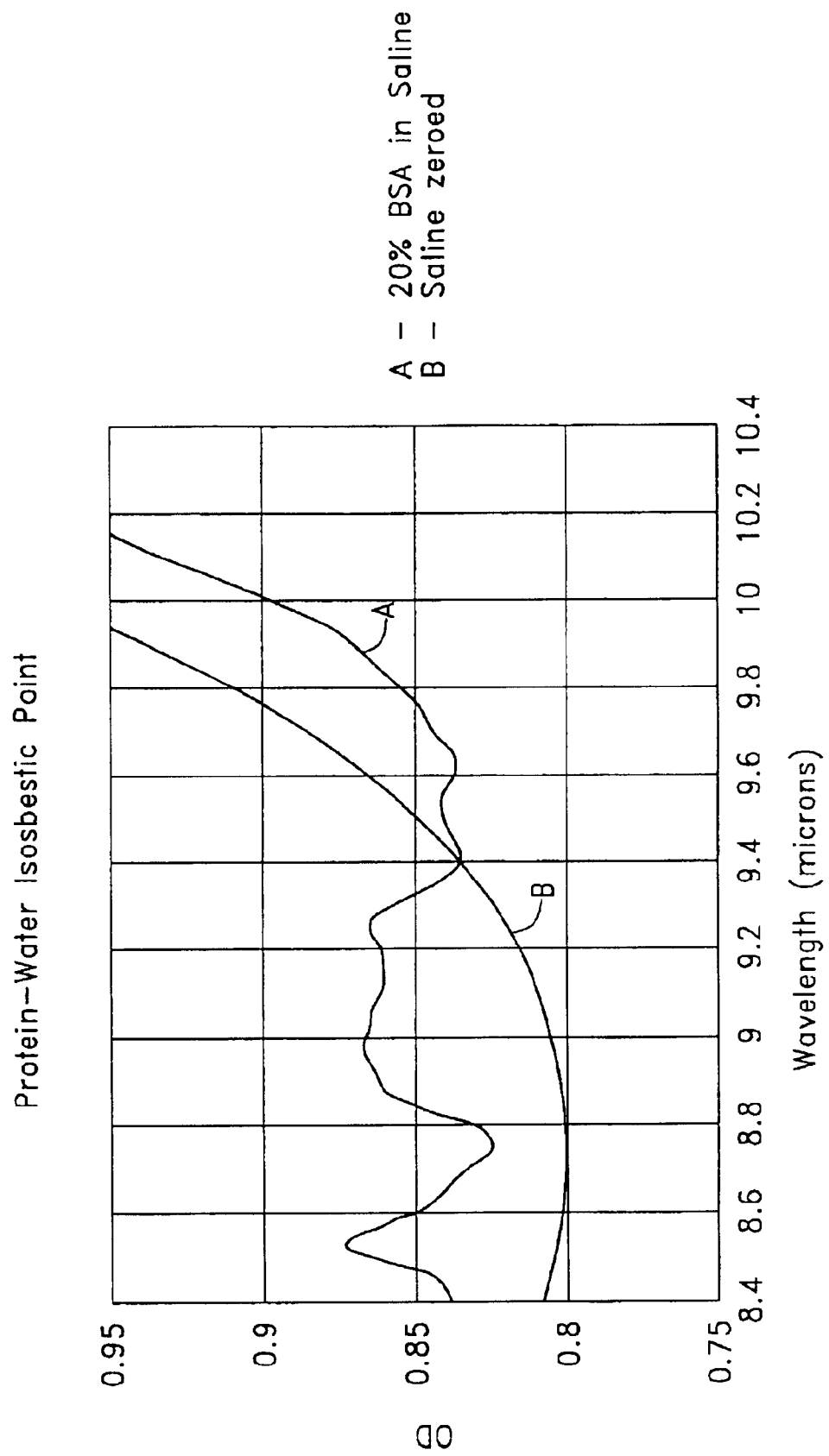

FIGS. 7A and 7B are graphs of the absorption spectra for 20% BSA in saline and for saline alone in two wavelength ranges. As can be seen in FIG. 7A, BSA protein and water exhibit identical infrared absorptions at an isosbestic wavelength of approximately 4.05 microns. Similarly, as can be seen in FIG. 7B, BSA protein and water exhibit identical infrared absorptions at an isosbestic wavelength of approximately 9.4 microns. The isosbestic wavelengths can be different for different proteins in different solutions.

Because the measured absorption of the protein and water are identical at the isosbestic wavelength, the measured absorption at the isosbestic wavelength is independent of the ratios of the protein concentration and the water concentration (hemocrit level). At an isosbestic wavelength, for a given sample volume, the same amount of absorption would be observed whether the sample 30 was entirely water, entirely protein, or some combination of the two. The absorption at the isosbestic wavelength is then an indication of the total sample volume, independent of the relative concentrations of water and protein. Therefore, the observed absorption at an isosbestic wavelength is a measure of the pathlength of the sample 30 only. In certain embodiments, the observed absorption at an isosbestic wavelength can be useful for measuring the effective optical pathlength for a sample 30. Additionally, such information can be used in subsequent calculations for compensation of instrument-related pathlength nonlinearities. In certain embodiments, these measurements can be made before or concurrently with absorption measurements in other wavelength ranges.

In certain embodiments, the observed absorption at an isosbestic wavelength can be useful for internally referencing absorption data by shifting the absorption spectrum to a selected value (such as 0, 0.5, 1, etc.) at the isosbestic wavelength by adding or subtracting a constant offset value across the entire wavelength spectral data set. In addition, the shifting of the absorption spectrum can be performed nonlinearly (e.g., shifting the portions of the absorption spectrum in different wavelength ranges by different amounts).

In certain embodiments, the selected absorption wavelength range for the shifting of the absorption spectrum in the operational block 300 of FIG. 5 comprises an isosbestic wavelength at which water and a whole blood protein have approximately equal absorptions. In certain embodiments in which the sample 30 comprises blood, the selected absorption wavelength range comprises wavelengths between approximately 3.8 microns and approximately 4.4 microns. In certain other embodiments, the selected absorption wavelength range comprises wavelengths between 9 microns and approximately 10 microns. Shifting the absorption spectrum such that the absorption is set to some value (e.g. 0) at a protein-water isosbestic point preferably helps remove the dependence on hemocrit level of the overall spectrum position relative to zero.

In certain embodiments, the absorption spectrum from the sample 30 is shifted in the operational block 300 so that the absorption baseline approximately equals a selected absorption value which is approximately equal to zero. In other embodiments, the selected absorption value is nonzero (e.g., 0.5 or 1). FIG. 1A is an exemplary absorption plot for a blood sample produced according to this technique.

Figure 8:
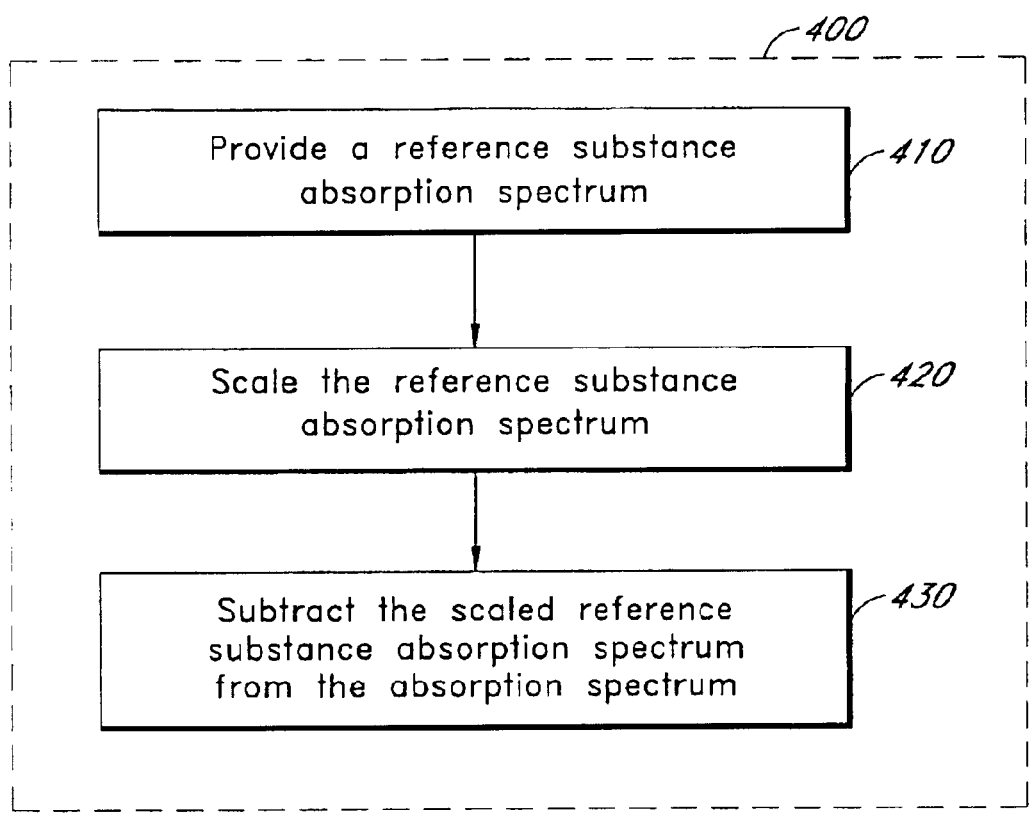
FIG. 8 is a flow diagram of an embodiment for subtracting the substance contribution.

Once a shifted absorption plot has been generated, such as the plot shown in FIG. 1A, the process of measuring a glucose concentration continues by subtracting one or more contributions to the absorption spectrum from other substances in the blood that interfere with the detection of the glucose. FIG. 8 is a flow diagram of an embodiment for subtracting the substance contribution in the operational block 400 of FIG. 5. In an operational block 410, a reference substance absorption spectrum is provided. In an operational block 420, the reference substance absorption spectrum is scaled by multiplying it by a scaling factor. In an operational block 430, the scaled reference substance absorption spectrum is subtracted from the measured absorption spectrum. This procedure thus preferably provides the corrected absorption spectrum which is substantially free of a contribution from the substance.

As described above, the main contributor to the IR absorption spectrum of blood in this wavelength range is water. Examination of the relative IR absorption spectra of water, hemoglobin, and glucose (illustrated in FIGS. 9A, 9B, and 9C) shows that the absorption peak at about 4.7 microns is due primarily to the presence of water. Thus, the height of this peak in the measured absorption spectrum from a blood sample can be used in conjunction with the reference pure water spectrum to determine the absorption of the sample due to the presence of water across the entire 4–11 micron range.

Figure 9A:
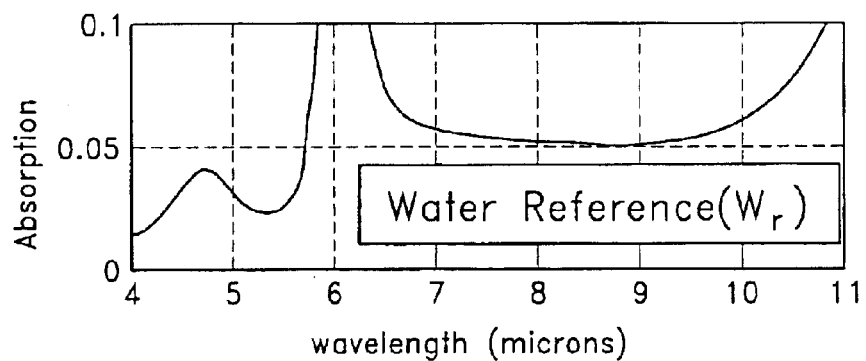
FIGS. 9A–C illustrate the relative infrared absorption spectra for water, hemoglobin, and glucose, respectively.
Figure 10:
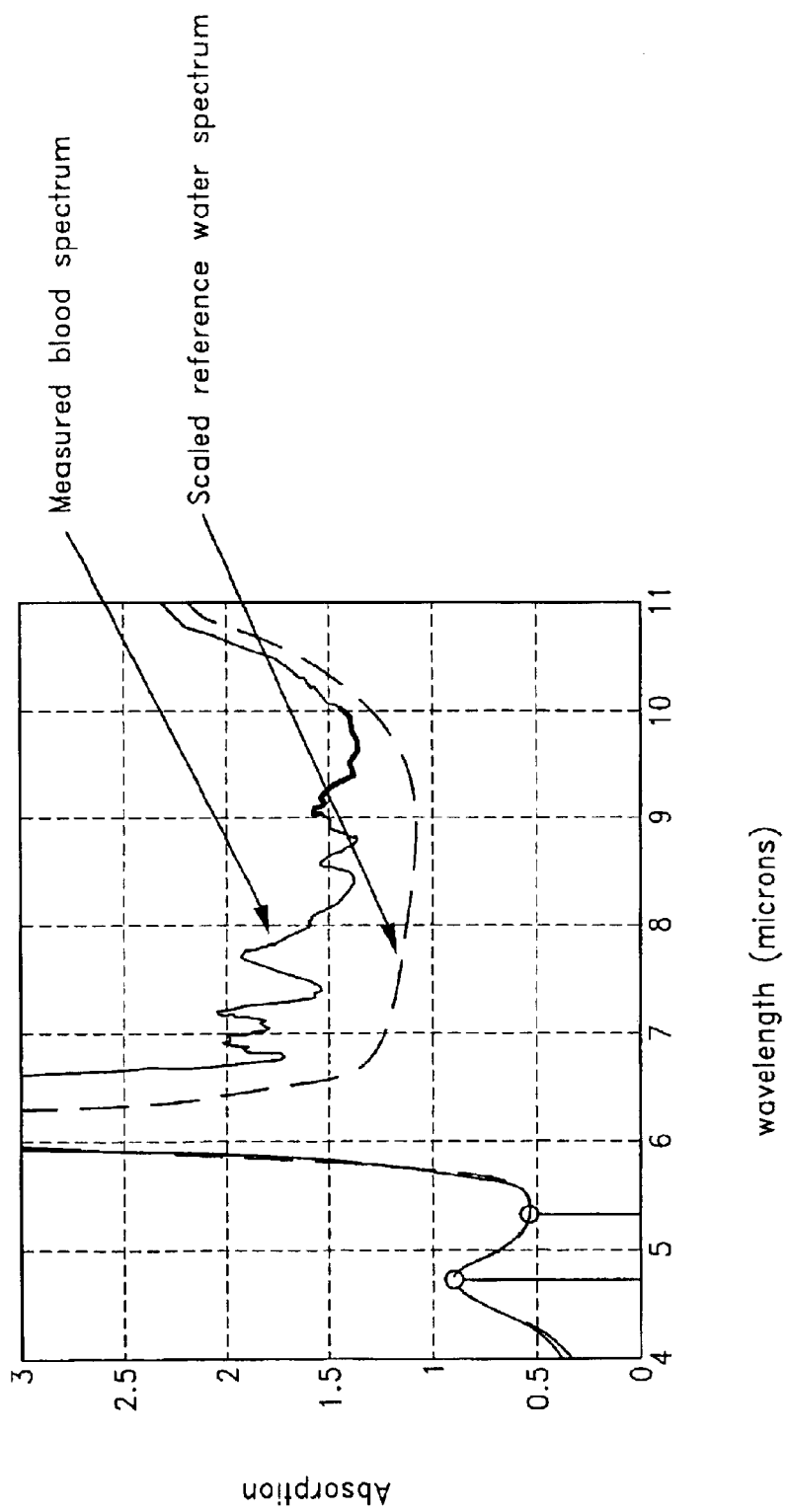
FIG. 10 is a graph illustrating the scaling procedure in an exemplary embodiment.
Figure 11:
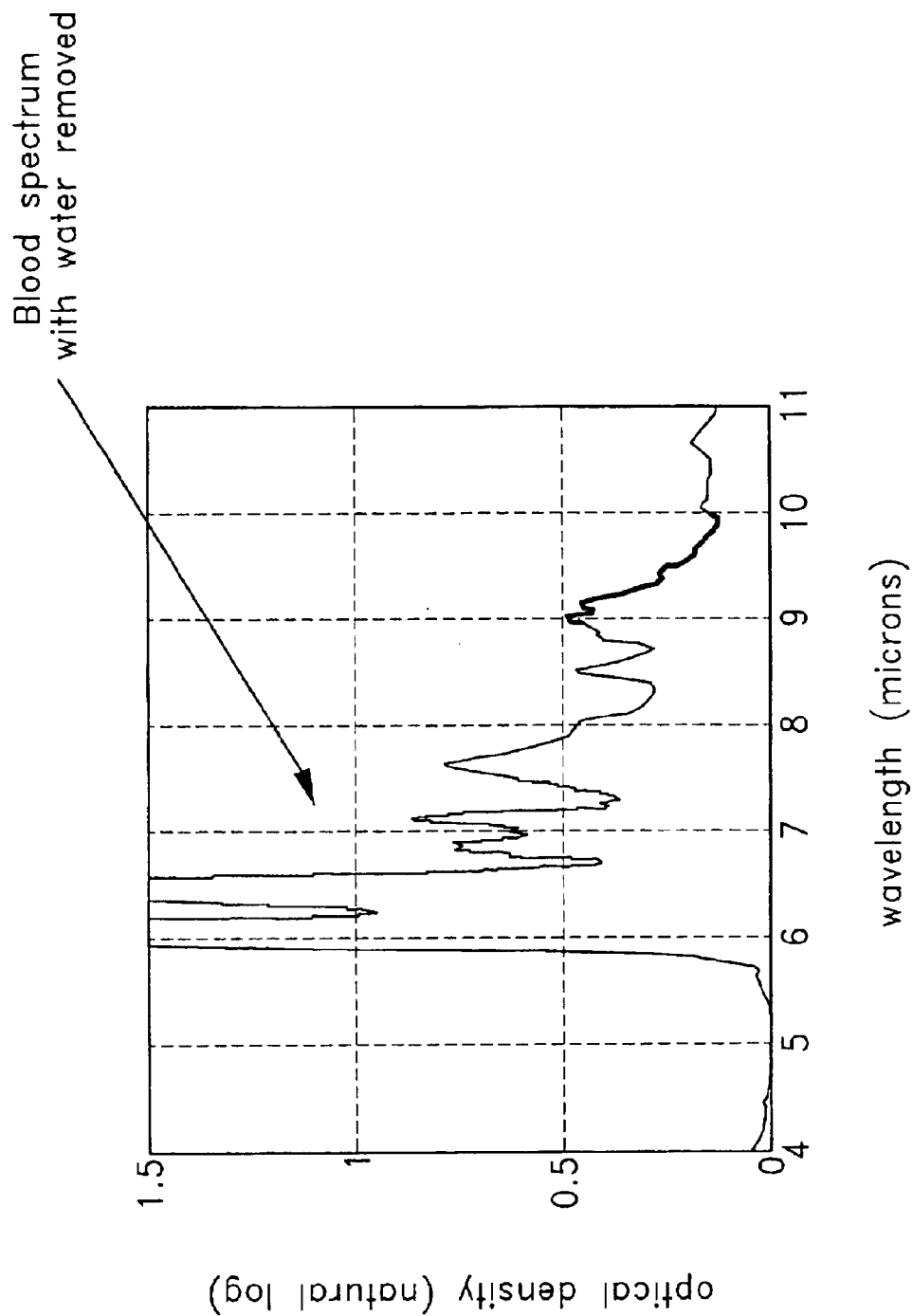
FIG. 11 is a graph illustrating the subtraction of the scaled reference water absorption spectrum of FIG. 11 from the measured absorption spectrum of FIG. 10.

To perform this subtraction in an exemplary embodiment, the reference absorption spectrum of water, such as the one shown in FIG. 9A, is provided and the values of the reference absorption spectrum are multiplied by a constant scale factor to scale the reference absorption spectrum by making the vertical height of the scaled reference peak from 4.7 microns to 5.2 microns equal to the peak height difference of the sample spectrum between 4.7 microns and 5.2 microns. The vertical position of the reference spectrum is then shifted in wavelength to align the scaled reference peak and trough at 4.7 microns and 5.2 microns with the same peak and trough on the measured blood spectrum. FIG. 10 shows the water reference spectrum manipulated in this way and overlaid with the measured sample absorption spectrum. At each wavelength, the scaled water reference value is subtracted from the measured sample absorption value. The result of this calculation, illustrated in FIG. 11, is an absorption spectrum of the measured sample With the contribution of water absorption subtracted. The resultant absorption spectrum is approximately equal to zero for wavelengths between approximately 4.5 microns and 5 microns. The resulting absorption spectrum is preferably effectively free of contributions from water absorption. Other scaling procedures, wavelength ranges, and subtraction procedures are compatible with embodiments described herein to produce the water-corrected absorption spectrum.

Figure 12:
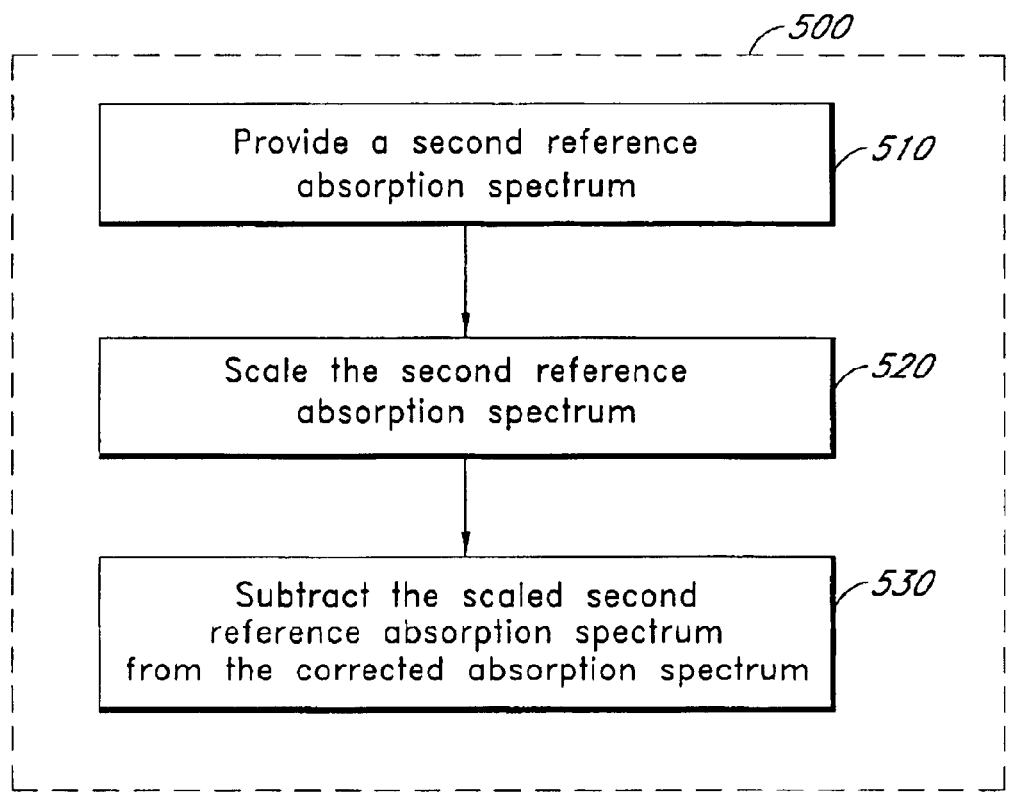
FIG. 12 is a flow diagram of an embodiment of subtracting a second contribution of a second substance.

In certain embodiments, the processing of the measured absorption spectrum continues by subtracting the contribution of a second substance (e.g., hemoglobin). FIG. 12 is a flow diagram of an embodiment of subtracting the second contribution of the second substance in an operational block 500. In an operational block 510, subtracting the second contribution comprises providing a second reference absorption spectrum corresponding to the second substance. In an operational block 520, subtracting the second contribution further comprises scaling the second reference absorption spectrum by multiplying the second reference absorption spectrum by a second scaling factor. The scaled second reference absorption spectrum approximately equals the corrected absorption spectrum at a second selected wavelength. In an operational block 530, subtracting the second contribution further comprises subtracting the scaled second reference absorption spectrum from the corrected absorption spectrum. Thus, a twice-corrected absorption spectrum is provided which is substantially free of contributions from the substance and from the second substance.

Figure 9B:
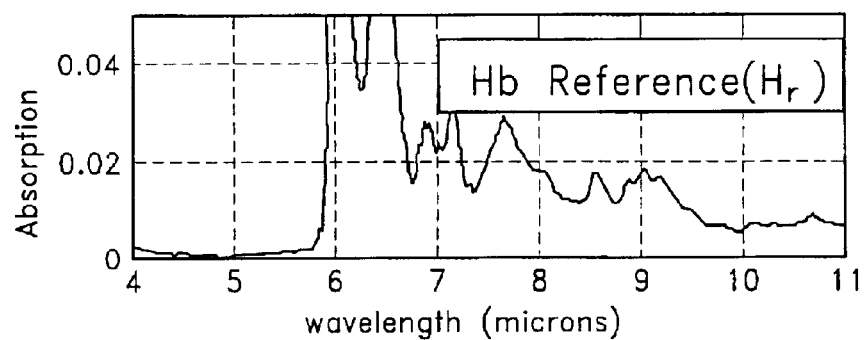
Figure 9C:
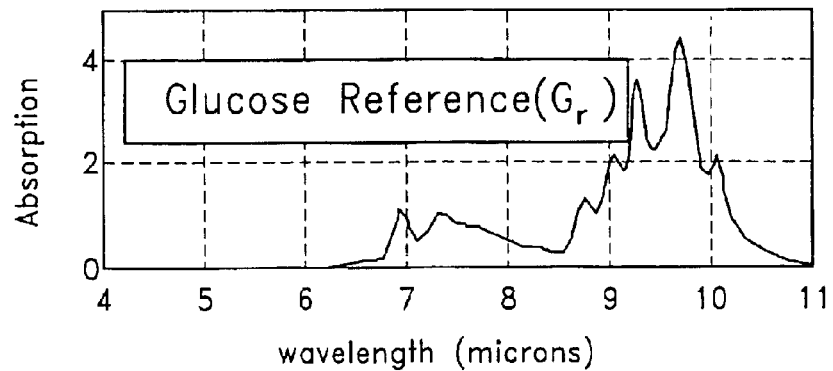

In certain embodiments, the sample comprises more than one substance. The method 100 of certain such embodiments further comprises subtracting the absorption contributions of these additional substances from the measured absorption spectrum. As illustrated in FIG. 9B, hemoglobin has significant absorption in the wavelength range of about 4–11 microns. The hemoglobin contribution to the measured absorption spectrum of a blood sample can be removed by providing and scaling a reference hemoglobin absorption spectrum and subtracting the scaled reference hemoglobin spectrum from the water-corrected measured spectrum.

Figure 13A:
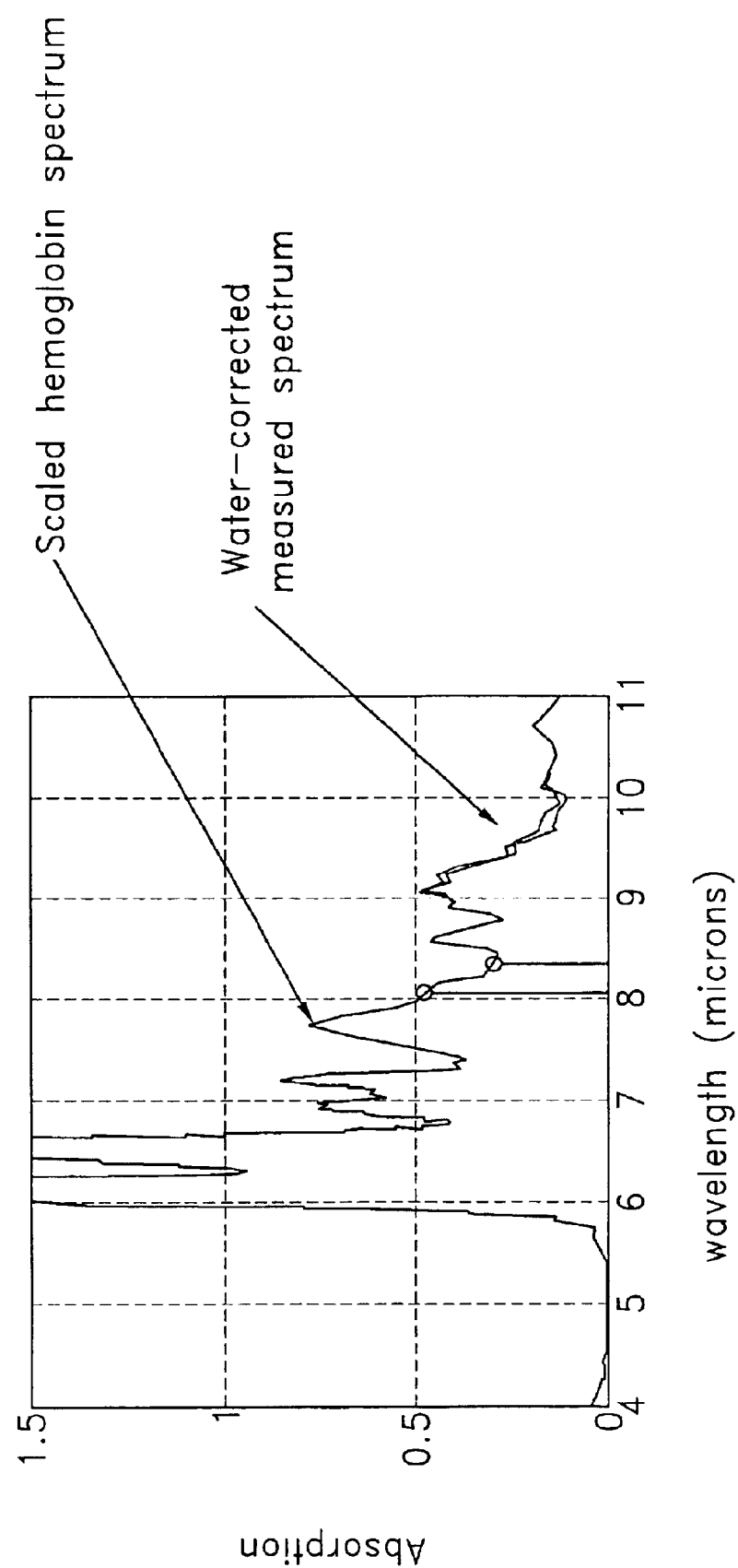
FIG. 13A is a graph of the water-corrected absorption spectrum overlaid with a scaled hemoglobin absorption spectrum.
Figure 13B:
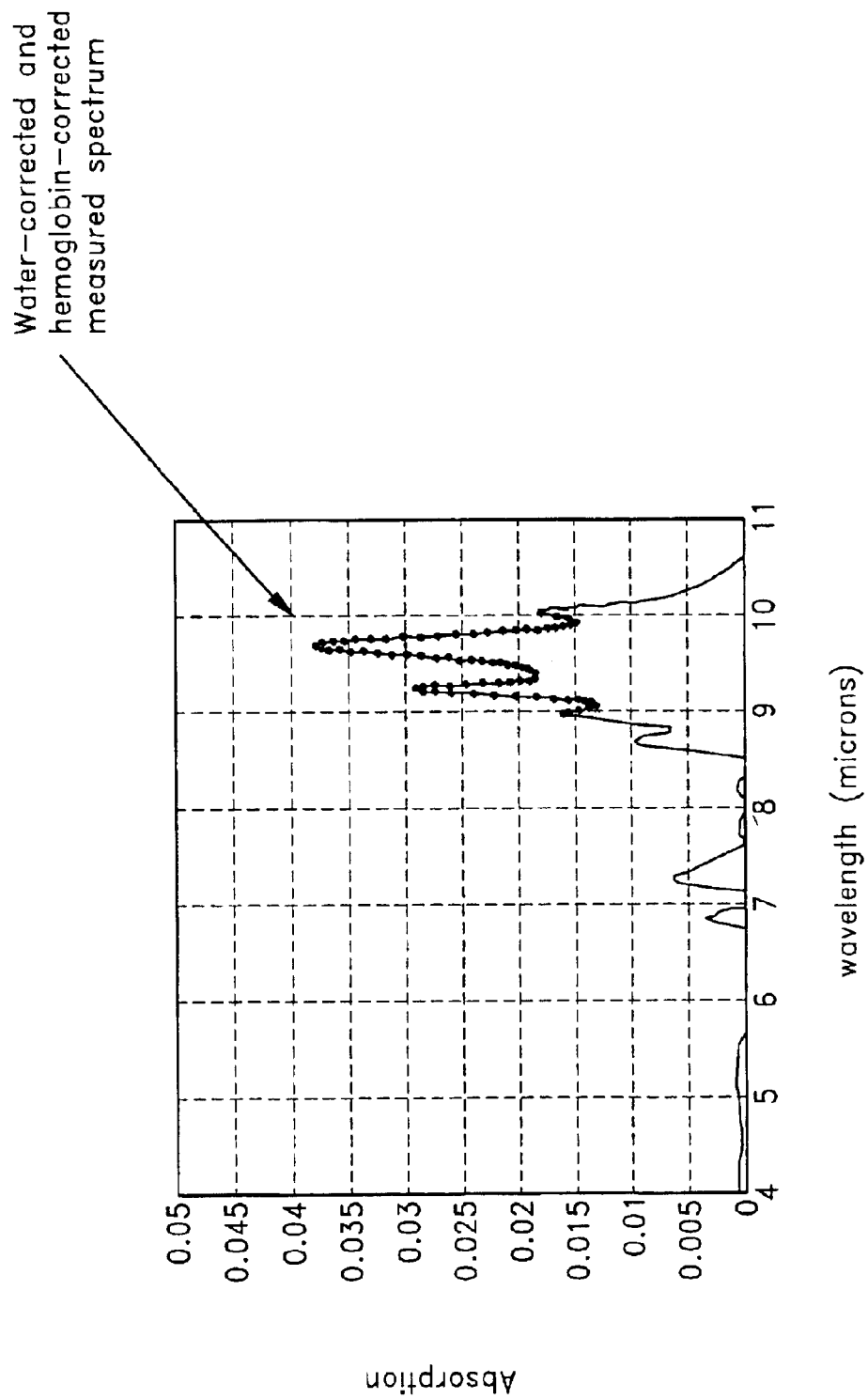
FIG. 13B is a graph of the resultant absorption spectrum after subtracting the scaled hemoglobin absorption spectrum from the water-corrected absorption spectrum.

To perform this subtraction in an exemplary embodiment, the reference hemoglobin spectrum, such as the one shown in FIG. 9B, is provided and multiplied by a constant scaling factor to scale the reference hemoglobin spectrum such that the absoption difference between about 8.0 to 8.4 microns of the scaled reference spectrum is equal to the absorption difference in the sample spectrum between about 8.0 to 8.4 microns. FIG. 13A shows the scaled reference hemoglobin spectrum overlaid with the water-corrected measured spectrum. At each wavelength, the scaled hemoglobin reference value is subtracted from the water-corrected measured spectrum value. The result of this calculation, illustrated in FIG. 13B, is an absorption spectrum of the measured sample with the contributions of water and hemoglobin absorption subtracted. Other scaling procedures, wavelength ranges, and subtraction procedures are compatible with embodiments described herein to produce the water-corrected and hemoglobin-corrected measured absorption spectrum.

For samples comprising blood, the second substance can comprise various compounds, examples of which include, but are not limited to, a whole blood protein, urea, and lactate.

Figure 14A:
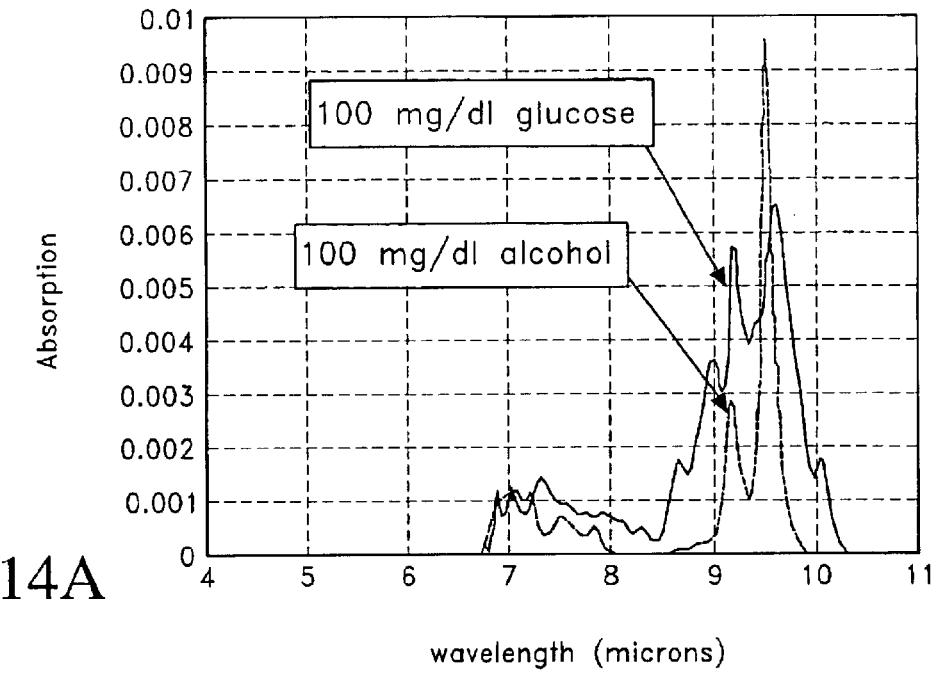
FIG. 14A shows the absorption spectra for pure alcohol and pure glucose.
Figure 14B:
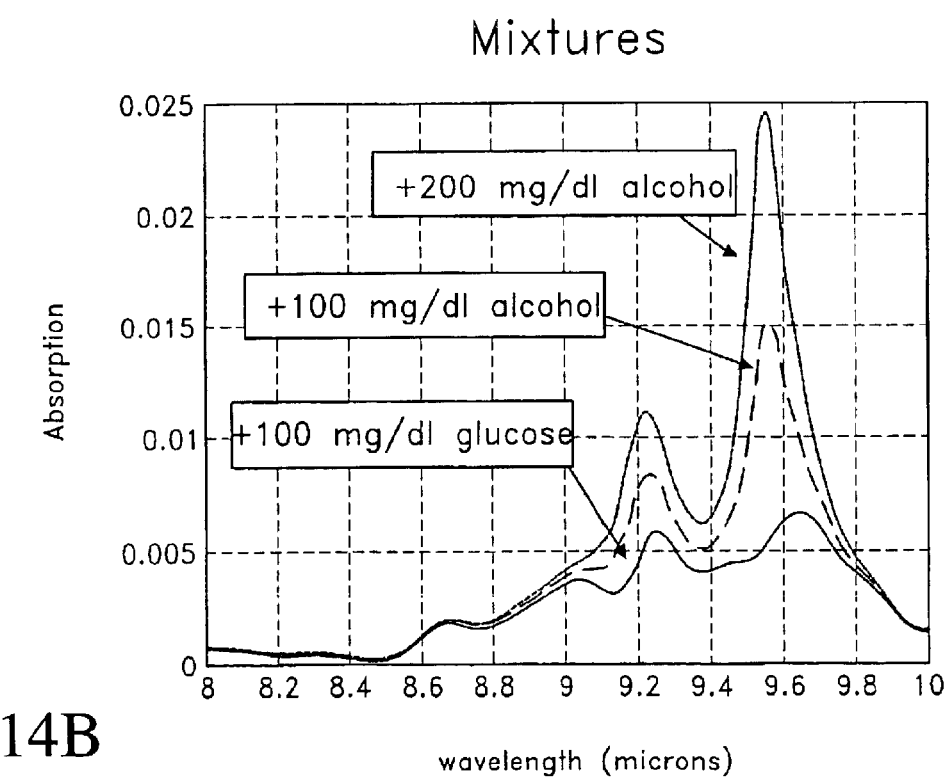
FIG. 14B shows the absorption spectra for 100 mg/dl of glucose and for mixtures of alcohol and glucose of (100 mg/dl glucose+100 mg/dl alcohol) and (100 mg/dl glucose+200 mg/dl alcohol).
Figure 15A:
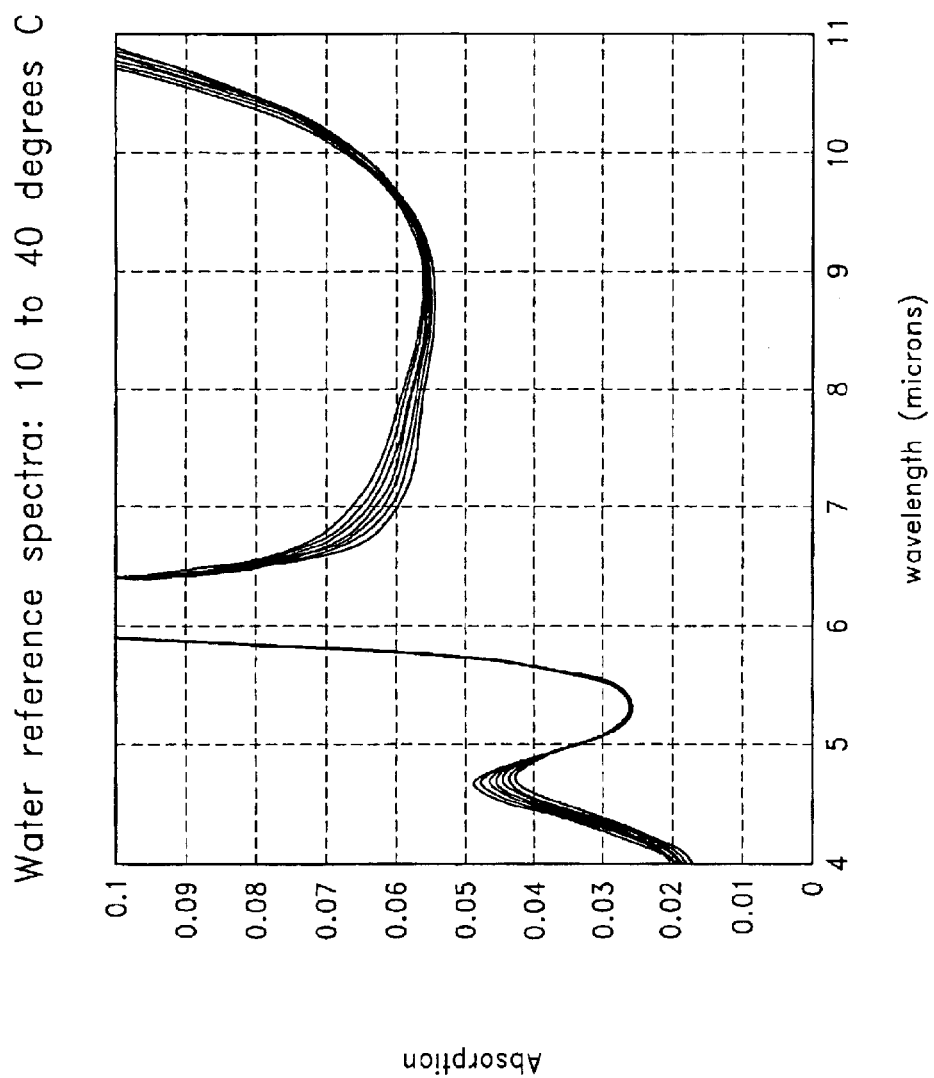
FIGS. 15A and 15B are graphs illustrating the temperature-dependence of the absorption spectrum of water.

In certain embodiments, the measured absorption spectrum can be further corrected for other contributions which are not due to the analyte of interest. FIG. 15A illustrates the absorption spectrum of pure alcohol as compared to the absorption spectrum of pure glucose. Alcohol is a potentially interfering substance with the glucose measurement because the absorption of alcohol is similar to that of glucose in the wavelength range of interest. It is observed that the peak height ratio of the peak at about 9.6 microns to the peak at about 9.2 microns for pure glucose is approximately 1.1–1.2, and the ratio for pure alcohol is approximately 3.0–3.2. As shown in FIG. 14B, this ratio of peak heights varies between these two values for absorption spectra for mixtures of glucose and alcohol. Thus, it is possible to use the peak height ratio to determine the relative concentrations of alcohol and glucose. The contribution from alcohol can then be subtracted from the measured absorption spectrum.

The correct subtraction of the water contribution to the total spectrum is affected by temperature also because the absorption spectrum of water changes with temperature changes. It is therefore advantageous for the system to store several different water reference spectra, with each one applicable to a selected temperature range. The appropriate reference would be selected for scaling and subtraction based on the temperature of the sample.

In some embodiments, hardware such as thermocouples, heaters, and the like may be provided to directly measure or control the temperature of the sample. Although this approach may be suitable at times, it can be difficult to accurately measure and control the blood temperature as the sample size is very small, and the actual blood temperature may vary from the cuvette temperature or the ambient temperature surrounding the cuvette.

Figure 15B:
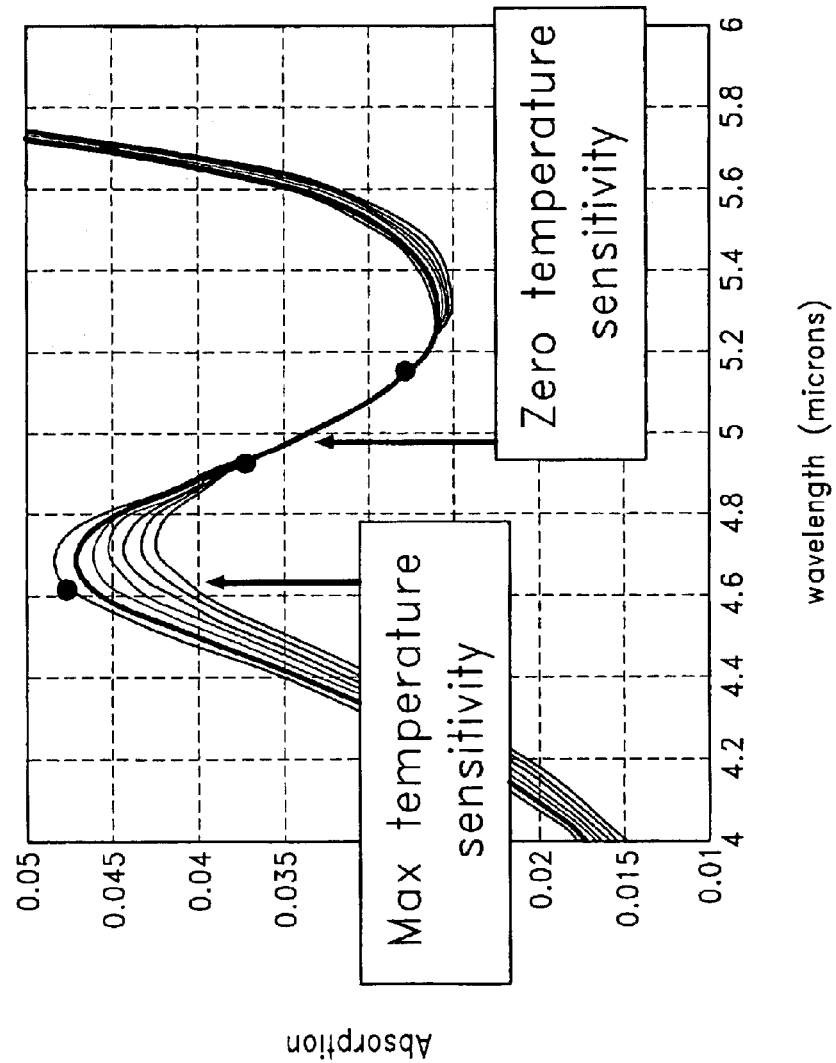

As illustrated in FIGS. 15A and 15B, this problem can alternatively be addressed by analyzing the sample spectrum itself, because different parts of the water absorption spectrum are affected by temperature by different amounts. FIG. 15B shows a close up of the peak and trough structure in the water spectrum between 4 and 6 microns that is used as described above to characterize the water contribution to the total blood spectrum. As shown in this Figure, the absorbance difference between about 4.9 microns and 5.15 microns is not very dependent on temperature, whereas the absorbance difference between 4.65 microns and 4.9 microns is highly temperature dependent. As temperature changes for a given sample with constant water concentration, the absorbance difference between 4.65 and 4.9 microns will change a lot, and the absorbance difference between 4.9 and 5.15 microns will not change much at all. Thus, the ratio of the absorbance difference between two points having high temperature dependence (e.g. 4.65 and 4.9 microns) to the absorbance difference between two points having low temperature dependence (e.g. 4.9 and 5.15 microns) can be used as a measure of temperature. Once this measurement is made, an appropriate selection from several different stored water reference curves can be made.

In certain embodiments in which the method 100 is practiced using a microprocessor, the reference substance absorption spectrum is stored in a memory device coupled to the microprocessor. In such embodiments, the memory device provides the stored reference substance absorption spectrum to the microprocessor in response to appropriate commands.

In certain embodiments, the reference substance absorption spectrum is provided by correcting a stored spectrum for wavelength nonlinearities. For example, where the substance comprises water, knowledge of the optical pathlength (based on the total sample absorption at one or more isosbestic wavelengths) as well as the measured absorption at one or more wavelengths dominated by water absorption (e.g., between approximately 4.5 and 5 microns) can be used to correct a stored reference water absorption spectrum for wavelength nonlinearities across the spectrum. Such corrections of the stored reference spectrum are advantageous for reducing distortions in the final results.

The second substance of certain embodiments comprises components of a boundary layer between water and a whole blood protein. Features in the measured absorption spectrum due to components of the boundary layer arise from interactions between the water and whole blood protein. These spectral features are ascribed to "bound" components.

In certain embodiments, free protein has an absorption peak centered around 7.1 microns, which can be used to correct the measured absorption spectrum for free protein. The contribution due to hydrated protein across the measured absorption spectrum can be corrected by subtracting the appropriate scaled reference absorption, such that the corrected absorption spectrum is approximately zero for a selected range of wavelengths. In certain embodiments, the range of wavelengths is between about 7.0 and 7.2 microns, or alternatively between 7.9 and 8.1 microns, or alternatively at a combination of wavelength ranges.

In certain embodiments, prior knowledge of optical pathlength based on total sample absorption at an isosbestic wavelength, as well as on total protein absorption in a selected wavelength range (e.g., 7.0–7.2 microns, or 7.9–8.1 microns) allows for the modification of a reference protein absorption spectrum that is compensated for nonlinearities. Such a modified reference protein absorption spectrum can be advantageous for distortion-free presentation of the resulting absorption spectrum.

Figure 16A:
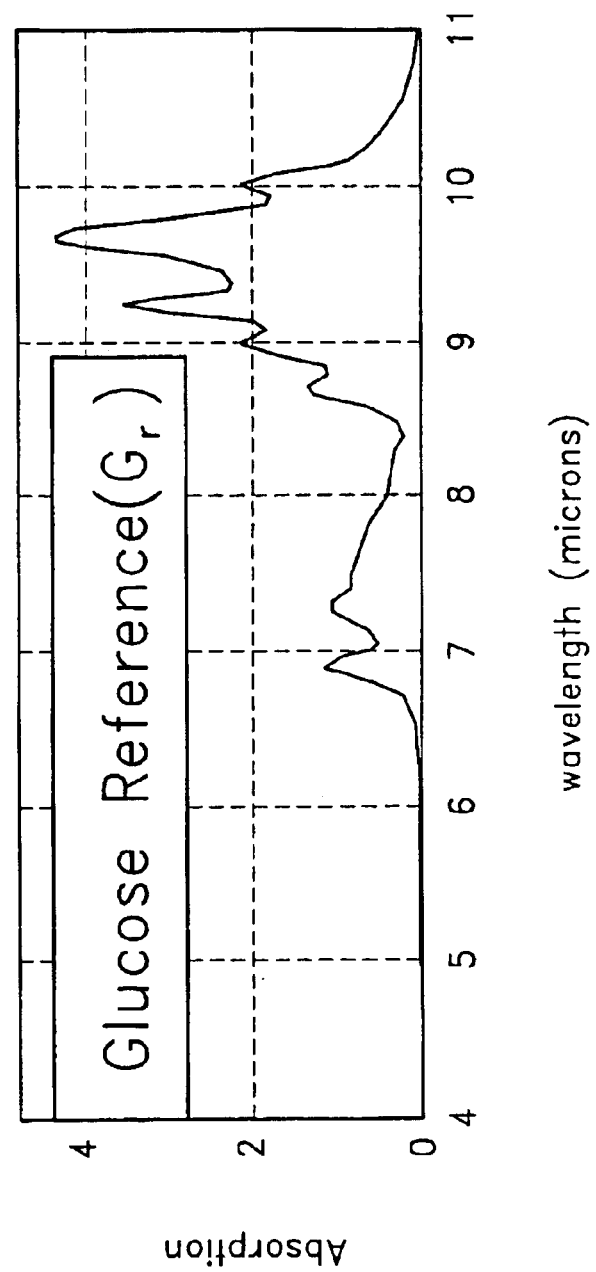
FIG. 16A is a graph of reference spectral data from the absorption spectrum of glucose.
Figure 16B:
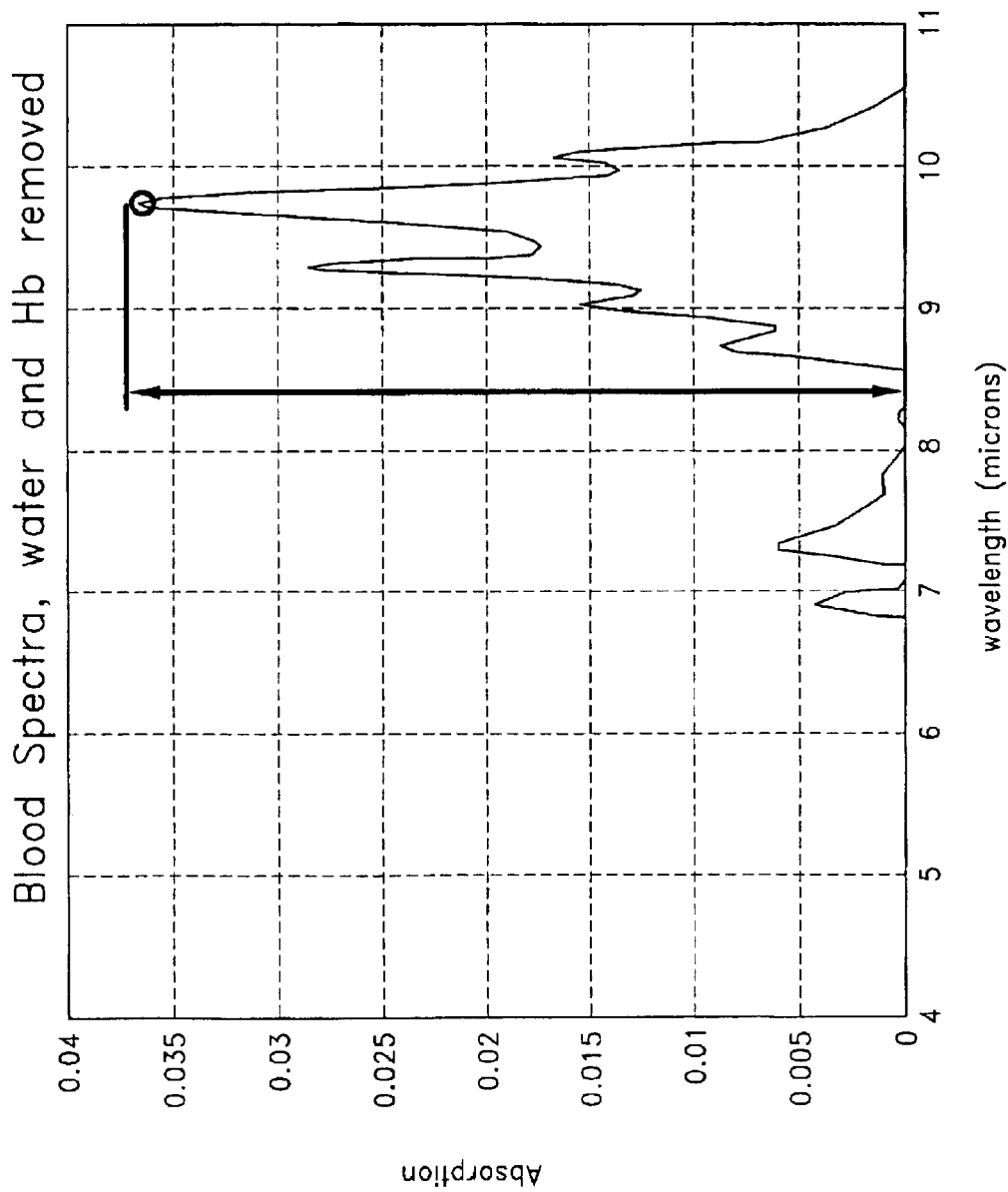
FIG. 16B illustrates an exemplary measurement made from the corrected absorption spectrum of FIG. 13B.

In certain embodiments, after correcting the measured absorption spectrum for contributions of one or more substances, the corrected absorption spectrum is fitted with reference analyte spectral data to provide a measure of the analyte concentration. The reference analyte spectral data can include data at a wavelength near an analyte absorption maximum. As an illustrative example, FIG. 16A shows a graph of reference spectral data from the absorption spectrum of glucose. The glucose spectrum includes various peaks, with the two largest peaks at wavelengths of approximately 9.25 and 9.65 microns, respectively. FIG. 16B illustrates an exemplary measurement made from the corrected absorption spectrum of FIG. 13B. The absorption difference of the corrected absorption spectrum between a wavelength of about 8.5 microns and a wavelength of approximately 9.65 microns provides a measure of the glucose concentration in the blood sample. Following the definition of glucose in blood (i.e., a measure of glucose per volume of the sample), a useful measure for glucose concentration is preferably obtained from algorithmically-derived infrared quantities, as described herein, by dividing the final glucose quantity by total water, total protein, or alternatively a combination of both.

Figure 17:
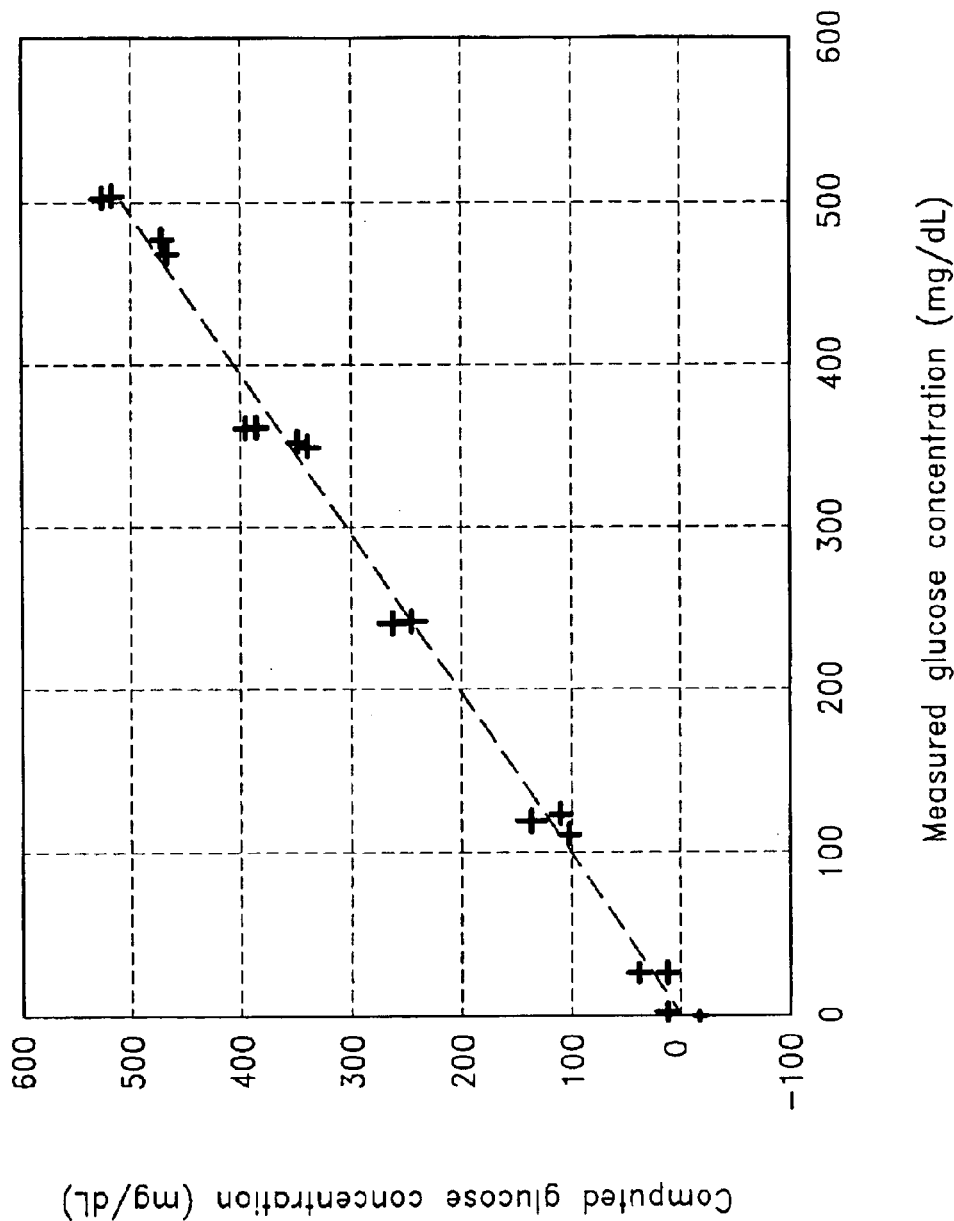
FIG. 17 is a graph of the calculated glucose concentration plotted against the glucose concentration determined using an immobilized enzyme biosensor analyzer.
Figure 18:
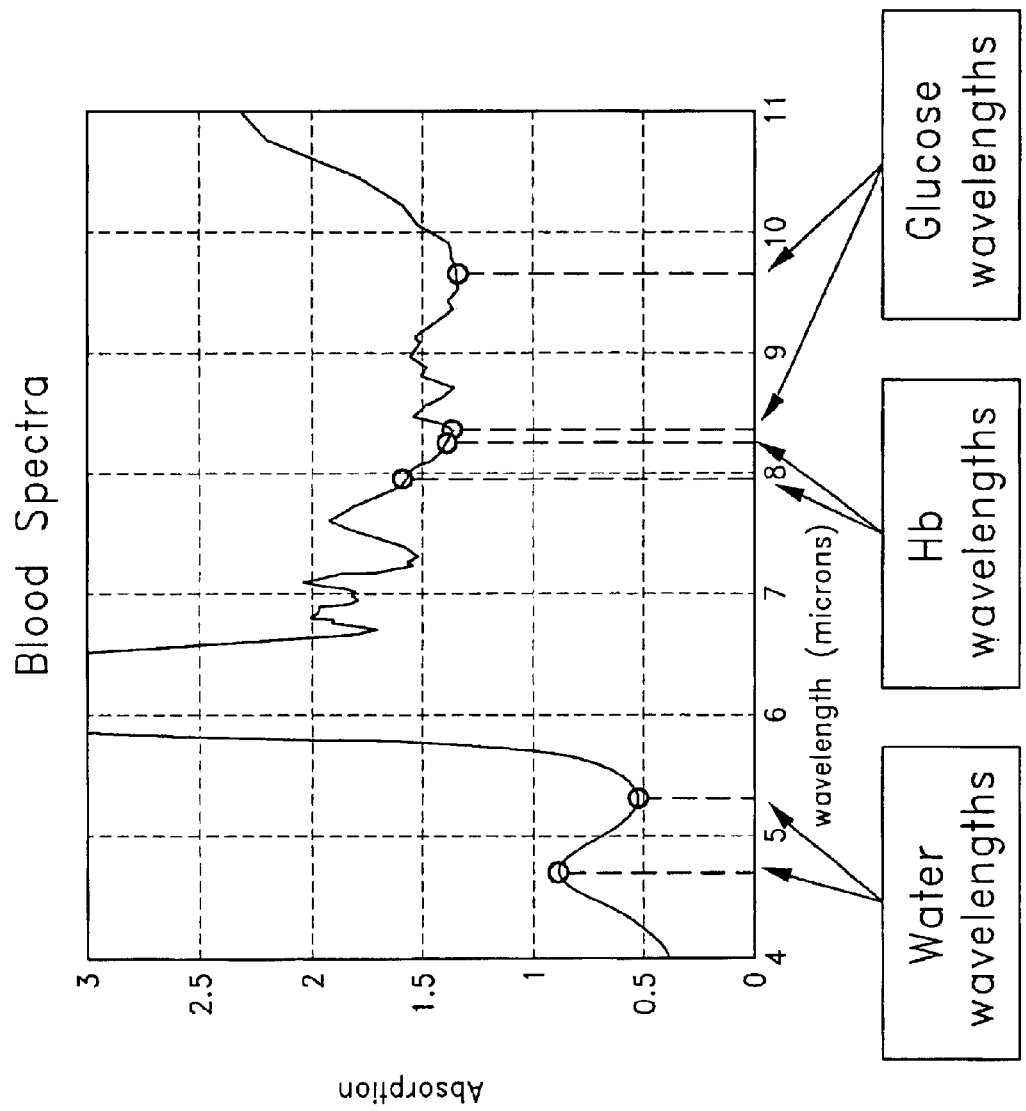
FIG. 18 is a whole blood absorption spectrum illustrating selected wavelengths which can be used in accordance with an embodiment of the present invention.

FIG. 17 is a graph of the computed glucose concentration of a blood sample plotted against the glucose concentration measured using a standard immobilized enzyme biosensor analyzer from YSI Life Sciences of Yellow Springs, Ohio. The plot shows good agreement between the present method and the YSI measurements.

Although the above discussion focuses on data sets comprising measurements over the entire range of IR wavelengths, it will be appreciated that it is not necessary to obtain data across the entire spectrum, but only at the discrete wavelengths used in the analysis. In the embodiment above, where water and hemoglobin contributions are subtracted from a whole blood spectrum to find glucose concentration, as little as ten or fewer total measurements are needed.

To characterize the water contribution, measurements at about 4.7 microns and 5.3 microns may be obtained. For characterizing hemoglobin, measurements at about 8.0 and 8.4 microns may be obtained. The glucose characterization may involve a measure of the difference between about 8.5 microns and 9.6 microns. This is six values, two for each component. In embodiments where it is desired to zero the transmittance curve and shift the absorbance values, it may be desirable to further make transmittance measurements at about the 6.1 micron water absorbance peak and the 4.1 micron water/protein isosbestic point. As described above, the addition of another data point at about 4.9 microns allows the determination of temperature. Another measurement at the lower alcohol peak of about 9.25 microns can be used to compensate the glucose measurement for alcohol content as well as is also described above.

This is a total of ten measurements, and each additional component to be subtracted may require one or two more each.

In certain embodiments, the resulting absorption spectrum (e.g., after being corrected for instrumental drift, optical pathlength, distortions, and contributions from major components) can be fitted with a reference glucose absorption spectrum to remove the glucose contribution. This absorption spectrum can be used further for individual determination of residual components. In certain embodiments, the residual components include high molecular weight substances, including but not limited to, other proteins, albumin, hemoglobin, fibrinogen, lipoproteins, and transferrin. In certain embodiments, the residual components include low molecular weight substances, including but not limited to, urea, lactate, and vitamin C. The final glucose measure can be corrected for the presence of such lower level potentially interfering substances by subtracting reference spectra of specific substances, such as urea, from the residual data.

Although described above in connection with particular embodiments of the present inventor, it should be understood that the descriptions of the embodiments are illustrative of the invention and are not intended to be limiting. Various modifications and applications may occur to those skilled in the art without departing from the true spirit and scope of the invention as defined in the appended claims.

What is claimed is:

1. A method of determining an analyte concentration in a sample, the sample comprising the analyte and a substance, the method comprising:

providing an absorption spectrum of the sample, the absorption spectrum having an absorption baseline, wherein providing the absorption spectrum comprises:
providing a transmittance spectrum of the sample, the transmittance spectrum having a transmittance baseline;
shifting the transmittance spectrum so that the transmittance baseline approximately equals zero in a selected transmittance wavelength range; and
determining the absorption spectrum from the transmittance spectrum;

shifting the absorption spectrum so that the absorption baseline approximately equals a selected absorption value in a selected absorption wavelength range; and subtracting a substance contribution from the absorption spectrum, thereby providing a corrected absorption spectrum substantially free of a contribution from the substance.

2. The method of claim 1, wherein providing the transmittance spectrum of the sample comprises:

transmitting at least a portion of an infrared signal through the sample, the infrared signal comprising a plurality of wavelengths; and measuring the portion of the infrared signal transmitted through the sample as a function of wavelength.

3. The method of claim 2, wherein providing the transmittance spectrum further comprises placing the sample in a cuvette.

4. The method of claim 1, wherein the sample comprises blood, the analyte comprises glucose, and the selected transmittance wavelength range comprises wavelengths at which the transmittance spectrum is dominated by water transmittance.

5. The method of claim 1, wherein the selected transmittance wavelength range comprises wavelengths between approximately 6 microns and approximately 6.15 microns.

6. The method of claim 1, wherein the selected transmittance wavelength range comprises wavelengths between approximately 12 microns and approximately 13 microns.

7. The method of claim 1, wherein the selected transmittance wavelength range comprises wavelengths approximately equal to 3 microns.

8. A method of determining an analyte concentration in a sample, the sample comprising the analyte and a substance, the method comprising:

providing an absorption spectrum of the sample, the absorption spectrum having an absorption baseline;

shifting the absorption spectrum so that the absorption baseline approximately equals a selected absorption value in a selected absorption wavelength range, wherein the sample comprises blood and the selected absorption wavelength range comprises an isosbestic wavelength at which water and a whole blood protein have approximately equal absorptions; and subsracting a substance contribution from the absorption spectrum, thereby providing a corrected absorption spectrum substantially free of a contribution from the substance.

9. The method of claim 8, wherein the selected absorption wavelength range comprises wavelengths between approximately 3.8 microns and approximately 4.4 microns.

10. The method of claim 8, wherein the selected absorption wavelength range comprises wavelengths between approximately 9 microns and approximately 10 microns.

11. The method of claim 8, wherein the whole blood protein comprises a material from the group consisting of: hemoglobin, albumin, globulin, and ferritin.

12. A method of determining an analyte concentration in a sample, the sample comprising the analyte and a substance, the method comprising:

providing an absorption spectrum of the sample, the absorption spectrum having an absorption baseline;

shifting the absorption spectrum so that the absorption baseline approximately equals a selected absorption value in a selected absorption wavelength range; and subtracting a substance contribution from the absorption spectrum, thereby providing a corrected absorption spectrum substantially free of a contribution from the substance, wherein subtracting the substance contribution comprises:

providing a reference substance absorption spectrum;

scaling the reference substance absorption spectrum by multiplying the reference substance absorption spectrum by a scaling factor; and subtracting the scaled reference substance absorption spectrum from the absorption spectrum, thereby providing the corrected absorption spectrum.

13. The method of claim 12, wherein the substance comprises water.

14. The method of claim 12, wherein the reference substance absorption spectrum is corrected for temperature-dependent effects.

15. The method of claim 12, wherein the reference substance absorption spectrum is corrected for wavelength nonlinearities.

16. The method of claim 12, wherein scaling the reference substance absorption spectrum utilizes at least two wavelength ranges.

17. A method of determining an analyte concentration in a sample, the sample comprising the analyte, a substance, and a second substance, the method comprising:

providing an absorption spectrum of the sample, the absorption spectrum having an absorption baseline;

shifting the absorption spectrum so that the absorption baseline approximately equals a selected absorption value in a selected absorption wavelength range;

subtracting a substance contribution from the absorption spectrum, thereby providing a corrected absorption spectrum substantially free of a contribution from the substance; and subtracting a second contribution corresponding to the second substance from the corrected absorption spectrum, thereby providing a twice-corrected absorption spectrum substantially free of contributions from the substance and from the second substance, wherein subtracting the second contribution comprises:

providing a second reference absorption spectrum corresponding to the second substance;

scaling the second reference absorption spectrum by multiplying the second reference absorption spectrum by a second scaling factor; and subtracting the scaled second reference absorption spectrum from the corrected absorption spectrum, thereby providing the twice-corrected absorption spectrum.

18. The method of claim 17, wherein the second substance comprises a whole blood protein.

19. The method of claim 17, wherein the second substance comprises components of a boundary layer between water and a whole blood protein.

20. The method of claim 17, wherein the second substance comprises urea or lactate.

21. The method of claim 12, further comprising fitting the corrected absorption spectrum with analyte spectral data, thereby yielding a measurement of the analyte concentration in the sample.

22. The method of claim 12, wherein the corrected absorption spectrum is fitted with reference analyte spectral data.

23. The method of claim 22, wherein the corrected absorption spectrum is fitted with the reference analyte spectral data at a wavelength near an analyte absorption maximum.

24. The method of claim 23, wherein the analyte comprises glucose and the analyte absorption maximum corresponds to a wavelength of approximately 9.25 microns.

25. The method of claim 23, wherein the analyte comprises glucose and the analyte absorption maximum corresponds to a wavelength of approximately 9.65 microns.

26. A method of providing pathlength-insensitive measurements of blood constituents in a sample using infrared (IR) spectroscopy, the method comprising:

providing an absorption spectrum of the sample, the absorption spectrum having an absorption baseline; and shifting the absorption spectrum so that the absorption baseline approximately equals a selected absorption value in an absorption wavelength range comprising an isosbestic wavelength at which water and a whole blood protein have approximately equal absorptions.

27. A method of measuring a pathlength of a sample comprising a first component and a second component, the method comprising:

providing an absorption spectrum of the sample;

determining an absorption value of the absorption spectrum at an isosbestic wavelength at which the first component and the second component have approximately equal absorption; and calculating the pathlength from the absorption value.

28. A method of estimating a glucose concentration of a blood sample, the method comprising:

measuring sample absorption at a plurality of wavelengths between about 4 microns and 11 microns;

subtracting a contribution to said sample absorption due to the presence of water; and subtracting a contribution to said sample absorption due to the presence of hemoglobin.

* * * * *

UNITED STATES PATENT AND TRADEMARK OFFICE
CERTIFICATE OF CORRECTION

PATENT NO. : 6,862,534 B2
DATED : March 1, 2005
INVENTOR(S) : Bernhard B. Sterling et al.

It is certified that error appears in the above-identified patent and that said Letters Patent is hereby corrected as shown below:

<u>Title page,</u>
Item [75], Inventor, should read:
-- Bernhard B. Sterling, Danville, CA; James R. Braig, Piedmont, CA; Daniel S. Goldberger, Boulder, CO; Kenneth G. Witte, San Jose, CA. --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,862,534 B2
DATED : March 1, 2005
INVENTOR(S) : Bernhard B. Sterling et al.

It is certified that error appears in the above-identified patent and that said Letters Patent is hereby corrected as shown below:

Title page,
Item [75], Inventors, should read
-- Bernhard B. Sterling, Danville, VA; James R. Braig, Piedmont, CA; Daniel S. Goldberger, Boulder, CO; Kenneth G. Witte, San Jose, CA. --.
Item [56], References Cited, FOREIGN PATENT DOCUMENTS, delete
"EP 0 982 582 A1     8/1998"

Column 13,
Line 45, delete "substracting," and insert -- subtracting --.

Column 14,
Line 58, delete "claim 12," and insert -- claim 21 --.

Signed and Sealed this

Fourteenth Day of February, 2006

JON W. DUDAS
*Director of the United States Patent and Trademark Office*